United States Patent
Tas

(10) Patent No.: US 9,108,860 B2
(45) Date of Patent: Aug. 18, 2015

(54) SYNTHESIS OF AMORPHOUS CALCIUM PHOSPHATE OR POORLY CRYSTALLINE CALCIUM PHOSPHATE POWDERS BY USING CA METAL

(71) Applicant: Ahmet Cuneyt Tas, Urbana, IL (US)

(72) Inventor: Ahmet Cuneyt Tas, Urbana, IL (US)

(73) Assignee: AHMET CUNEYT TAS, Piscataway, NJ (US)

( * ) Notice: Subject to any disclaimer, the term of this patent is extended or adjusted under 35 U.S.C. 154(b) by 87 days.

(21) Appl. No.: 13/759,513

(22) Filed: Feb. 5, 2013

(65) Prior Publication Data

US 2013/0209377 A1    Aug. 15, 2013

Related U.S. Application Data

(60) Provisional application No. 61/597,267, filed on Feb. 10, 2012.

(51) Int. Cl.
| | | |
|---|---|---|
| C01F 11/18 | (2006.01) | |
| C01B 25/32 | (2006.01) | |
| A61L 27/12 | (2006.01) | |

(52) U.S. Cl.
CPC .............. *C01F 11/181* (2013.01); *A61L 27/12* (2013.01); *C01B 25/32* (2013.01); *C01F 11/18* (2013.01); *C01F 11/182* (2013.01); *A61L 2430/02* (2013.01); *A61L 2430/12* (2013.01); *C01P 2004/03* (2013.01); *C01P 2004/61* (2013.01)

(58) Field of Classification Search
None
See application file for complete search history.

(56) References Cited

U.S. PATENT DOCUMENTS

| 4,237,147 A * | 12/1980 | Merten et al. ................. 426/590 |
| 2006/0216247 A1 * | 9/2006 | Phillips ........................... 424/52 |
| 2009/0130150 A1 * | 5/2009 | Gazzaniga et al. ........... 424/401 |

OTHER PUBLICATIONS

P Layrolle, A Lebugle. "Characterization and Reactivity of Nanosized Calcium Phosphates Prepared in Anhydrous Ethanol." Chemistry of Materials, vol. 6, 1994, pp. 1996-2004.*
AC Tas. "Calcium metal to synthesize amorphous or cryptocrystalline calcium phosphates." Materials Science and Engineering C, vol. 32, 2012, pp. 1097-1106, available online Feb. 10, 2012.*
University of Arizona Department of Biology. http://www.biology.arizona.edu/biochemistry/problem_sets/ph/hh.html, accessed Nov. 26, 2013, 2 printed pages.*
T Stretton. Ka and pKa for Polyprotic acids. http://www2.ucdsb.on.ca/tiss/stretton/database/polyprotic_acids.htm, accessed Nov. 26, 2013, 1 printed page.*
SM Berge, LD Bighley, DC Monkhouse. "Pharmaceutical Salts." Journal of Pharmaceutical Sciences, vol. 66 No. 1, Jan. 1977, pp. 1-19.*
Bratsch, S. G., (1989) Standard Electrode Potentials and Temperature Coefficients in Water at 298.15K, J. Phys. Chem. Ref. Data, 18(1), 1989, 21 pages.
Gaur, Swati et al. (2014) In Vitro investigation of biodegradable polymeric coating for corrosion resistance of Mg—6Zn—Ca alloy in simulated body fluid, Materials Science and Engineering C, 42, 91-101.
Eanes, et al. (1967) Amorphous Calcium Phosphate in Skeletal Tissues, Clinical Orthopedics and Related Research, 223-235.
Larson, P. R., et al. (2012) Non-stirred synthesis of Na- and Mg-doped, carbonated apatitic calcium phosphate, Ceramics International 39, 1485-1493.
Markovic, M., et al. (2004), Preparation and comprehensive characterization of a calcium hydroxyapatite reference material, J. Res. Natl. Inst. Stand. Technol., 109, 553-568.
Posner, et al. (1954), Defect apatite series in synthetic and natural calcium phosphates: the concept of pseudoapatites, Short Communications, Preliminary Notes, 15, 304-305.

* cited by examiner

*Primary Examiner* — Isaac Shomer

(57) ABSTRACT

The present invention relates to the synthesis of bioceramics, in particular, of amorphous or cryptocrystalline calcium phosphates.

6 Claims, 17 Drawing Sheets

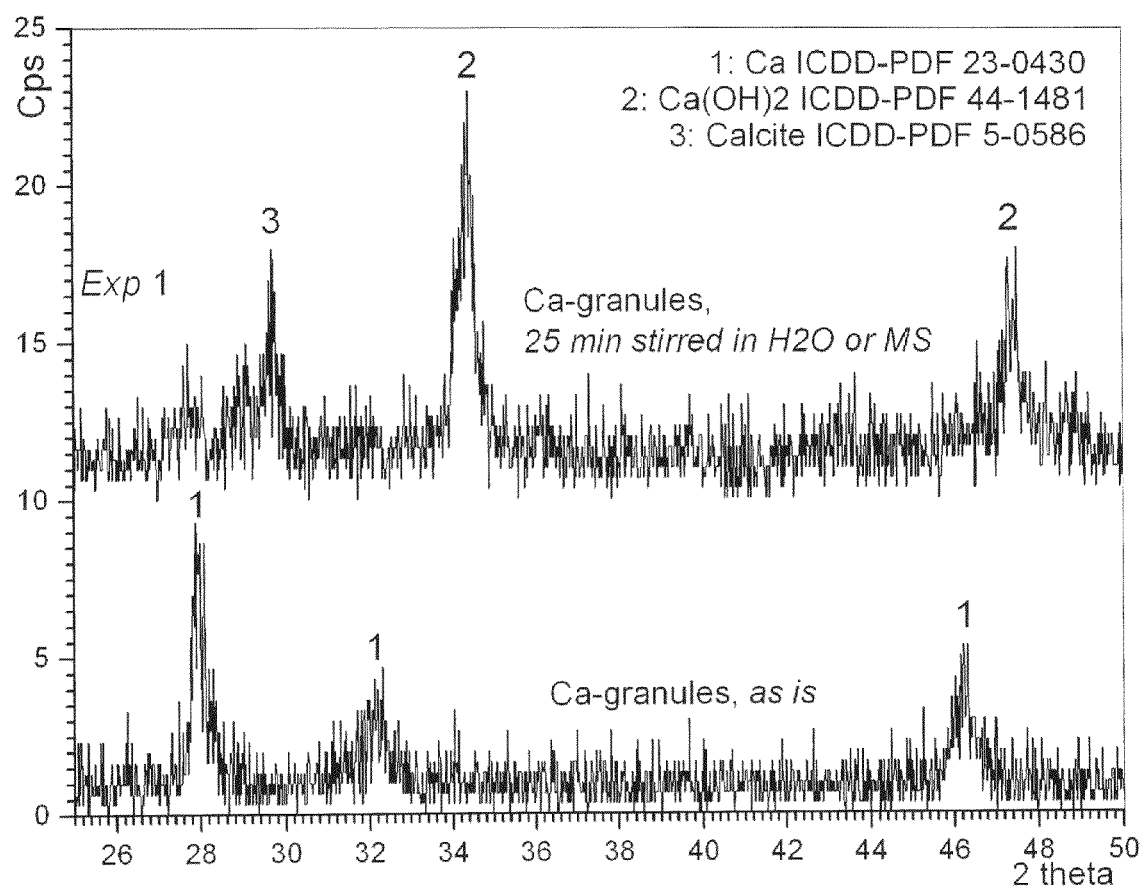

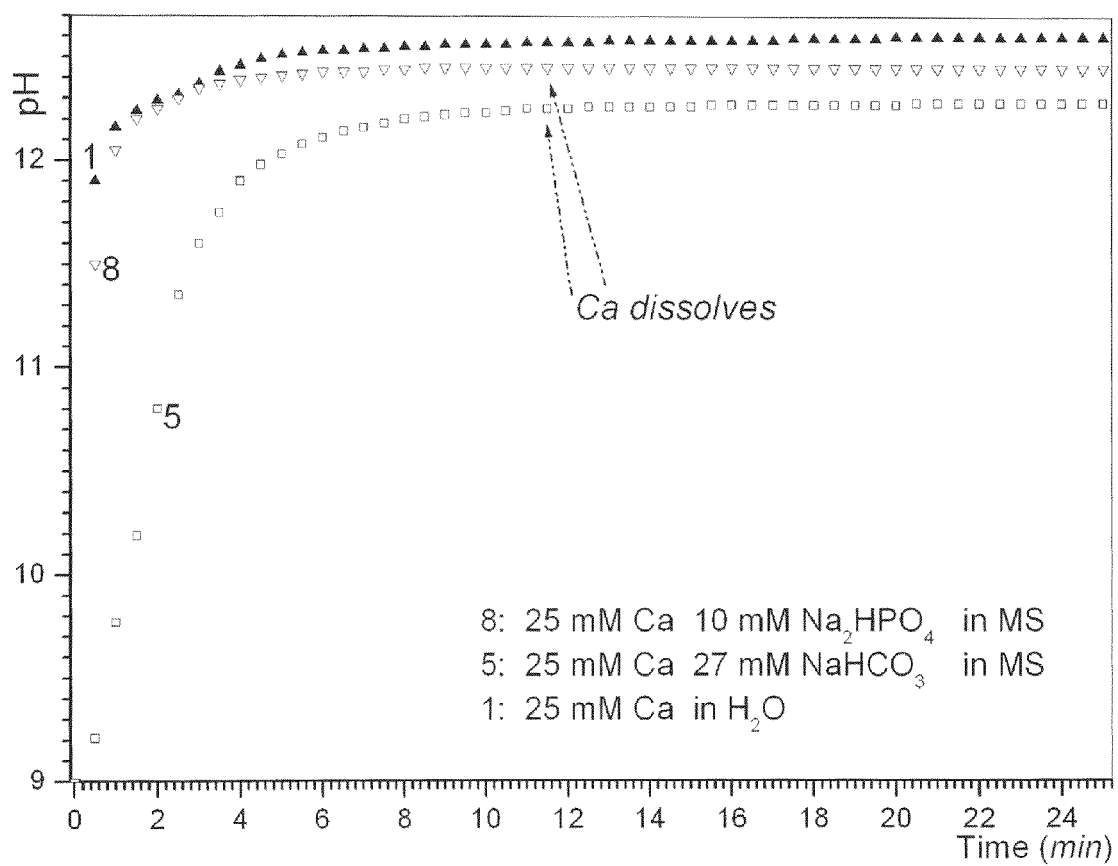

Figure 1B:
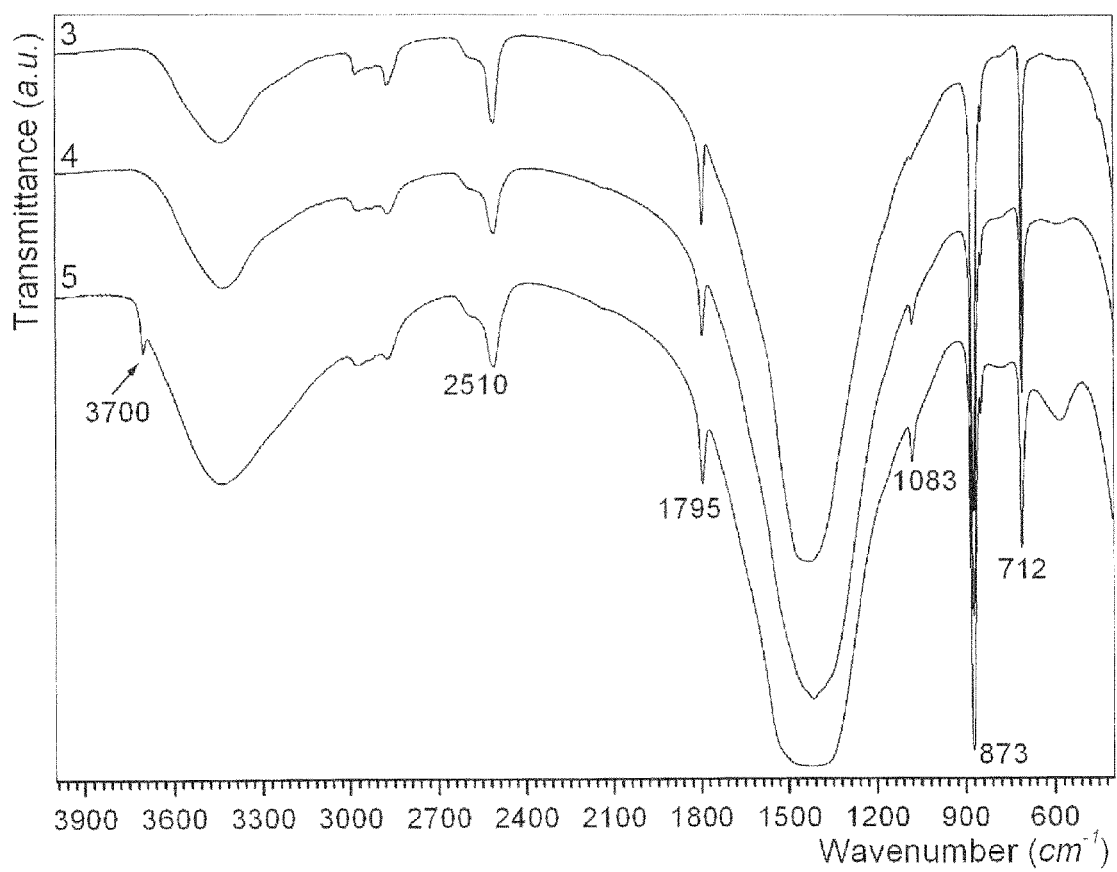

SYNTHESIS OF AMORPHOUS CALCIUM PHOSPHATE OR POORLY CRYSTALLINE CALCIUM PHOSPHATE POWDERS BY USING CA METAL

PRIOR RELATED APPLICATIONS

The present application claims the benefit of priority to U.S. Provisional Application No. 61/597,267 filed Feb. 10, 2012, which is incorporated by reference herein in its entirety.

The present invention relates to the synthesis of bioceramics, in particular, of amorphous or cryptocrystalline calcium phosphates.

The systematic synthesis and characterization of poorly crystallized (i.e., cryptocrystalline) apatite (PCA) powders in deionized (i.e., free of $Na^+$, $K^+$, $Mg^{2+}$, $Cl^-$ and $HCO_3^-$ ions) water solutions containing dissolved calcium nitrate tetrandyrate ($Ca(NO_3)_2 \cdot 4H_2O$) and diammonium hydrogen phosphate (($NH_4)_2HPO_4$) were initiated in the early 50's by Hayek and co-workers [E. Hayek, F. Muliner and K. Koller, "Zur Kenntnis des Hydroxylapatits", Monatsh. Chem. 82 (1951) 958-9691]. The work of Hayek et al. taught to raise the pH values of such cryptocrystalline apatite synthesis solutions to around 10.5-11 by the addition of ammonium hydroxide ($NH_4OH$). Still today, the Hayek method of synthesizing cryptocrystalline apatitic CaP powders is one of the most often used.

In the mid 50's, it was realized that the mineral of natural hard tissues consisted of non-stoichiometric pseudoapatites. Posner and co-workers [N. C. Blumenthal, J. M. Holmes and A. S. Posner, "Effect of preparation Conditions on the Properties and Transformation of Amorphous Calcium Phosphate", Mater, Res. Bull. 7 (1972) 1181-1190)] described to prepare synthetic amorphous calcium phosphate (ACP) powders by using $CaCl_2$- and $(NH_4)_2HPO_4$-containing distilled water solutions (i.e., water solutions not containing ions such as $Na^+$, $Mg^{2+}$, $K^+$ or $HCO_{3-}$) whose pH values were raised to around 11 by $NH_4OH$ additions.

ACP consists of roughly spherical clusters (also called Posner clusters) close to 1 nm in diameter, with a Ca/P molar ratio of 1.5 and the formula of $Ca_9(PO_4)_6$, which are free of water. Synthetic ACP, according to Posner et al. [F. Betts and A. S. Posner, "An X-ray Radial Distribution Study of Amorphous Calcium Phosphate", Mater. Res. Bull. 9 (1974) 353-360], consisted of roughly spherical $Ca_9(PO_4)_6$ clusters, which formed in water and were then aggregated randomly to produce larger spherical particles of ACP with the inter-cluster space being filled with water.

ACP, when in contact with an aqueous solution, is known to exhibit the unique ability to first nucleate OCP (octacalcium phosphate, $Ca_8(HPO_4)_2 \cdot 5H_2O$)-like nanosize crystallites on the surfaces of its particles, which would then rapidly mature into apatitic calcium phosphate. This property of ACP powders was successfully exploited to prepare injectable orthopedic cements [A. Tofighi, S. Mounic, P. Chakravarthy, C. Rey, and D. Lee, "Setting Reactions Involved in Injectable Cements based on Amorphous Calcium Phosphate," Key Eng. Mat. 192-1 (2000) 769; D. D. Lee, C. Rey, M. Aiolova, and A. Tofighi, "Method of Preparing a Poorly Crystalline Calcium Phosphate and Methods of Its Use," U.S. Pat. No. 7,517,539 Apr. 14, 2009]. Posner and his co-workers were also the first to study the interaction of casein micelles of bovine milk with ACP powders [T. C. A. McGann, R. D. Kearney, W. Buchheim, A. S. Posner, F. Betts, and N. C. Blumenthal, "Amorphous Calcium Phosphate in Casein Micelles of Bovine Milk," Calcified Tissue Int. 35 (1983) 821], and this apparently led to the development of ACP-casein phosphopeptide (CPP) [M. Bannon, R. H. Hammond, and E. C, Reynolds, "Amorphous Calcium Phosphate-Casein Phosphopeptide (ACP-CPP) as a Dentinal Hypersensitivity Treatment Agent," J. Dent. Res. 74 (1995) 754] complexes for dental remineralizalion applications.

Since the early studies of Hayek and Posner no novel approaches to the synthesis of ACP powders were explored, i.e., meaning the calcium source employed in the synthesis processes was always selected from the Ca-chloride, Ca-nitrate and Ca-acetate salt group, and the pH values of the synthesis solutions were raised to the basic range (pH~11) by the addition of strong bases such as $NH_4OH$, $NaOH$ or $KOH$.

The starting materials used in said synthesis such as nitrate, acetate or ammonium ions as well as the process conditions such as raising the pH by adding strong bases, however, do not correspond to the conditions under which calcium phosphate is formed in the organism.

Therefore, it was an object of the present application to provide an improved method for the preparation of calcium phosphate powders.

According to the invention, said object is achieved by a method of preparing calcium phosphates and/or calcium carbonates or mixtures thereof, comprising metallic calcium as a starting material.

Herein, metallic calcium was used for the first time in synthesizing $CaCO_3$, poorly crystalline (cryptocrystalline) apatite (PCA) or x-ray amorphous calcium phosphate (ACP) powders. In particular, biomimetic amorphous calcium phosphate or poorly crystalline calcium phosphate powders are synthesized.

The use of metallic Ca eliminates the need for external pH control in the calcium phosphate synthesis solutions in the form of adding strong bases such as $NaOH$, $KOH$, $LiOH$ or $NH_4OH$.

The use of metallic Ca makes it possible to synthesize PCA or ACP powders in solutions completely free of foreign ions such as ammonium, nitrate or acetate, which are not encountered in human blood.

Calcium phosphate synthesis with metallic Ca can be performed both in pure water and in water containing ions found in human blood.

The present invention thus provides a simple process for the preparation of calcium phosphates, calcium carbonates or mixtures thereof, whereby the conditions at the same time can be adjusted so as to mimick naturally occurring conditions in biosynthesis of these compounds. In particular, starting compounds not present in organism but hitherto used in the preparation of ACP or PCA powders can be avoided using the method according to the invention. In particular, it is possible to synthesize CaP powders (either ACP or PCA) in aqueous solutions totally free of nitrate ($NO_3$), acetate ($CH_3COO$) or ammonium ($NH_4$) ions. These ions are not shown to be present in biological bone or tooth formation processes. Further, it is possible to synthesize ACP or PCA powders by using aqueous solutions having pH values from 9 to 12 (which was underlined by the early works of Hayek and Posner as a necessity) without even using the smallest aliquot of a strong base such as $NH_4OH$, $NaOH$, $KOH$ or $LiOH$.

In previous CaP synthesis, nitrate or acetate ions are introduced into the synthesis solutions by the use of calcium nitrate tetrahydrate or calcium acetate monohydrate as the calcium source. In contrast thereto, the use of Ca metal as the only calcium source allows for total elimination of any nitrate or acetate ions.

Thus, according to the invention, it is preferred to use calcium metal as the only calcium source, i.e. ≥90 wt %, more preferably ≥95 wt %, even more preferably ≥99 wt %, still more preferably ≥99.9 wt % and most preferably 100 wt % of the initial calcium present are present as Ca metal.

The metallic calcium is preferably in the form of pieces, wire or granules and in particular is the only source of calcium.

Ca metal can be produced by electrolysis of a molten bath of calcium chloride salt. Ca metal granules react with distilled water to raise its pH under a slow evolution of $H_2$ gas (i.e., in situ deprotonation). According to the invention, the use of Ca metal as the calcium source in ACP or PCA synthesis eliminates the need for using any strong bases in raising the solution pH to the desired levels of from at least 8, preferably at least 9 up to 13, preferably up to 12.

According to a preferred embodiment of the invention, the synthesis is performed in mineralization solutions which mimick the inorganic ion concentrations of body fluids, in particular, of human blood plasma. In this way, ACP or RCA powders are obtained which are most similar to the natural materials. In particular, biomimetic amorphous calcium phosphate or poorly crystalline calcium phosphate powders are obtained. Also in the organism, in particular, in the human body, no deionized or distilled water is used in synthesizing the mineralized portion of bone or teeth. Rather, different inorganic ions are present. Therefore, an inventive method is preferred which further comprises at least one of $Na^+$, $K^+$, $Mg^{2+}$, $Cl^-$, $HCO_3^-$ and $HPO_4^{2-}$ ions in the reaction solutions. Preferably, the concentrations of the inorganic ions present in the synthesis solutions are similar to the respective concentrations in biological fluids, in particular, in human blood plasma.

Besides metallic calcium, the inventive method for the preparation of calcium phosphates, in particular, for the preparation of amorphous calcium phosphate (ACP) or cryptocrystalline or polycrystallized apatite (RCA) preferably uses $HPO_4^{2-}$, $PO_4^{3-}$, $H_2PO_4^-$ or/and $H_3PO_4$, in particular, $HPO_4^{2-}$. For preparing calcium carbonates, preferably $HCO_3^-$, $CO_3^{2-}$ or/and $H_2CO_3$, in particular, $HCO_3^-$ is used besides metallic calcium. Preferably, the mentioned anions are used as sodium salts, with disodium hydrogen phosphate and sodium bicarbonate being especially preferred.

The inventive method is preferably performed in solution. Thereby, the starting materials are reacted in a solution, in particular, in aqueous solution, whereby the products precipitate from this solution.

The content of calcium metal is preferably 0.1 to 500 mM, preferably 0.2 to 100 mM and most preferably 0.25 to 50 mM.

The content of phosphate provided by $HPO_4^{2-}$, $PO_4^{3-}$, $H_2PO_4^-$ and $H_3PO_4$, in particular, by $HPO_4^{2-}$ is preferably 0.01 to 200 mM, in particular, 0.1 to 20 mM.

The content of carbon provided by $HCO_3^-$, $CO_3^{2-}$ and $H_2CO_3$, in particular, by $HCO_3^-$ is preferably 0.5 to 300 mM, in particular, 4 to 30 mM.

According to the invention it was found that the presence of chloride ions enhances the reaction of metallic calcium with aqueous solutions of phosphates and/or carbonates. Therefore, the inventive method is preferably carried out in the presence of chloride ions. The concentration of chloride ions is preferably 10 to 500 mM, in particular, 90 to 125 mM.

It was found that amorphous calcium phosphate (ACP), polycrystallized or cryptocrystalline apatite and/or calcium carbonate can be synthesized by the inventive method. Preferably, amorphous calcium phosphate (ACP) and/or polycrystallized or cryptocrystalline apatite are synthesized by the inventive method.

To obtain such materials which correspond as much as possible to naturally occurring or biosynthesized materials and, thus, may be named "biomimetic materials", it is preferred to add to the reaction medium also minerals occurring in the organism, in particular, in human blood serum. Therefore, besides a phosphorus source such as hydrogen phosphate and/or a carbon source such as bicarbonate, the reaction medium preferably additionally comprises at least one of sodium ions, potassium ions, magnesium ions, zinc ions, chloride and fluoride ions. Reaction media containing all of these ions are preferred. Reaction media containing sodium ions, potassium ions, magnesium ions and chloride ions in addition to hydrogen phosphate and/or bicarbonate ions are particularly preferred. Most preferred, the reaction medium comprises chloride ions.

Thereby, the amount of sodium ions is preferably 10 to 500 mM, in particular, 80-150 mM. The concentration of potassium ions preferably is 0.1 to 50 mM, in particular, 0.5 to 3 mM. The concentration of magnesium ions is preferably 0.1 to 50 mM, in particular, 1 to 5 mM. The concentration of zinc ions is preferably 20 to 50,000 ppm, in particular, 200 to 4,000 ppm. The concentration of chloride ions is preferably 10 to 500 mM, in particular, 90 to 125 mM. The concentration of fluoride ions is preferably 0.1 to 100, in particular, 1 to 10 ppm.

Preferred starting compounds for the synthesis solution of the present invention are sodium chloride, potassium chloride, magnesium chloride hexahydrate, sodium bicarbonate and disodium hydrogen phosphate.

A major advantage of the present invention is that no hydroxide base, in particular, no $NH_4OH$, $LiOH$, $NaOH$, $KOH$, $Mg(OH)_2$ and $Ca(OH)_2$ is added to the reaction medium. Still, the final solution pH is from pH 8 to pH 13, in particular, from pH 9 to pH 12.

According to the invention, the formation of calcium phosphate (CaP) can be initiated, for example, by addition of calcium metal, in particular, calcium metal granules or shots into a synthesis solution. The synthesis solution contains hydrogen phosphate ions and optionally preferably hydrogen carbonates, sodium, potassium, magnesium or/and chloride ions. For the formation of calcium carbonates preferably calcium metal, in particular, calcium metal granules, shots or wire are added into a synthesis solution comprising hydrogen carbonates and optionally preferably hydrogen phosphates, sodium, potassium, magnesium or/and chloride ions. The synthesis solution is preferably continuously stirred. The temperature is not critical, whereby operation over a broad range is possible, e.g. from >0° C. to 90° C., in particular, at 10° C. to 50° C. and more preferably at room temperature, i.e. 22±1° C. The synthesis reaction reaches completion in less than 30 minutes. The precipitated product powders can be obtained by separation from the solution.

The present invention also relates to calcium phosphates, calcium carbonates or mixtures thereof obtainable by the inventive method. In particular, the invention relates to amorphous calcium phosphate (ACP) powders, cryptocrystalline apatite (PCA) powders and calcium carbonate powders. Further, these inventive materials preferably comprise minerals also contained in the natural materials, in particular, $Na^+$, $K^+$, $Mg^{2+}$, $Cl^-$, $Zn^{2+}$ and/or $F^-$, preferably one or more of $Na^+$, $K^+$, $Mg^{2+}$, $Zn^{2+}$ and $F^-$.

The materials prepared according to the invention can be used for preparing biomaterials for orthopedic or bone defect-filling applications, for remineralization of enamel or for a preparation used in dental applications.

The invention is further illustrated by the attached Figures and the Examples given below.

The Figures show the following:

FIG. 1a XRD traces of as-received Ca granules (bottom) and Ca granules stirred in H2O or MS (top, Exp. 1)

FIG. 1b FTIR traces of the samples of experiments 3, 4, and 5

Figure 1C:
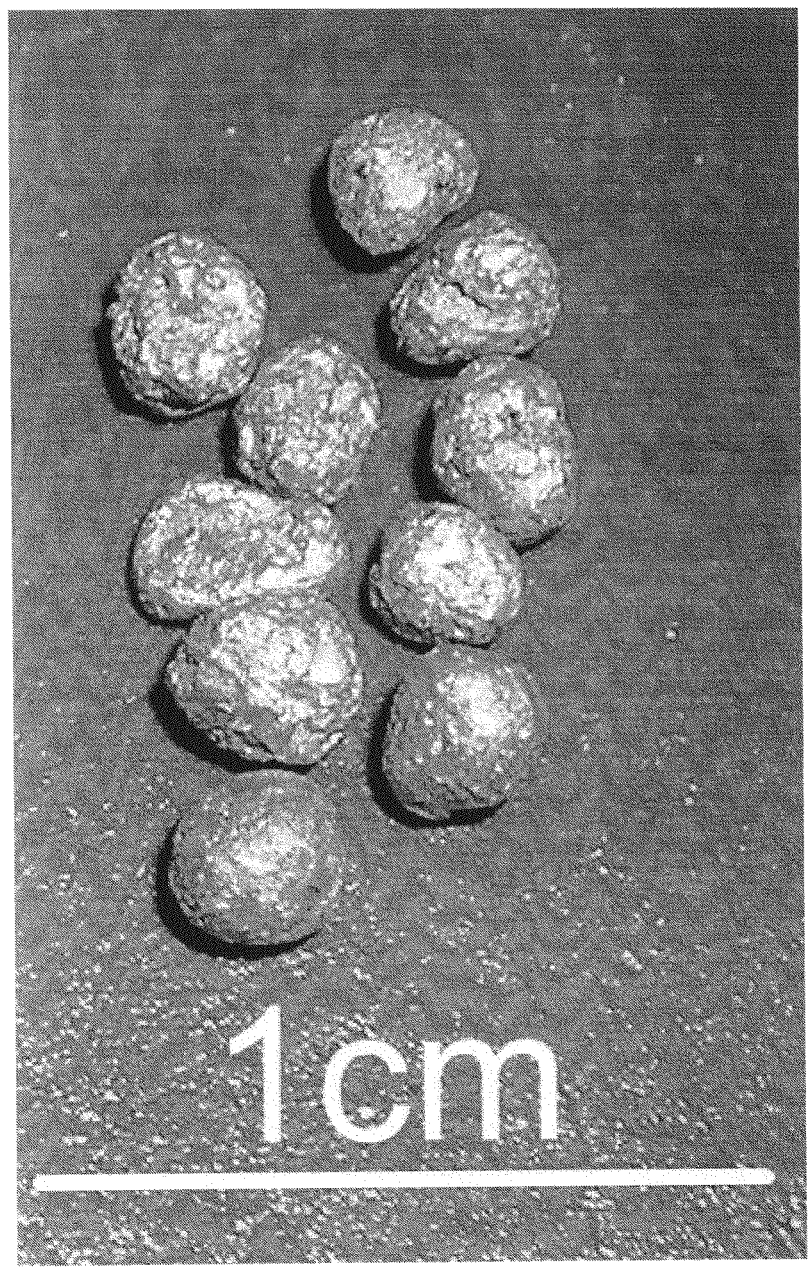

FIG. 1c Macrophotograph of as-received Ca metal granules (shots)

Figure 1D:
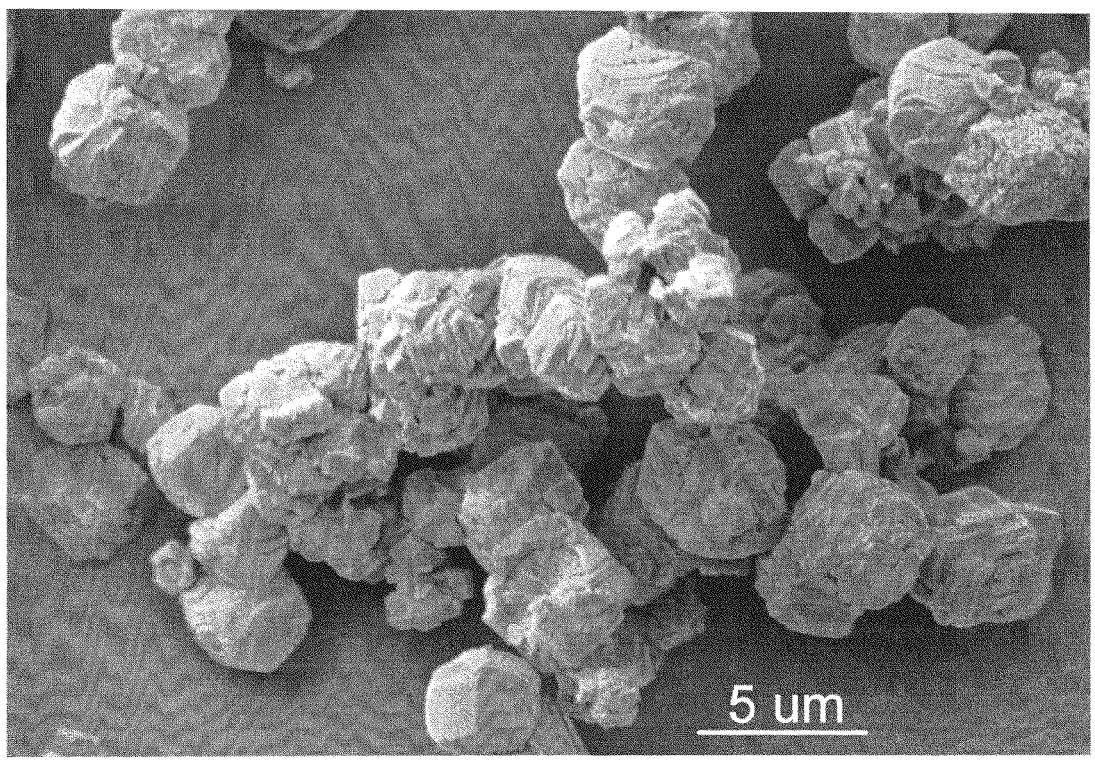

FIG. 1d SEM photomicrograph of the $CaCO_3$ samples of experiment 5

Figure 2:
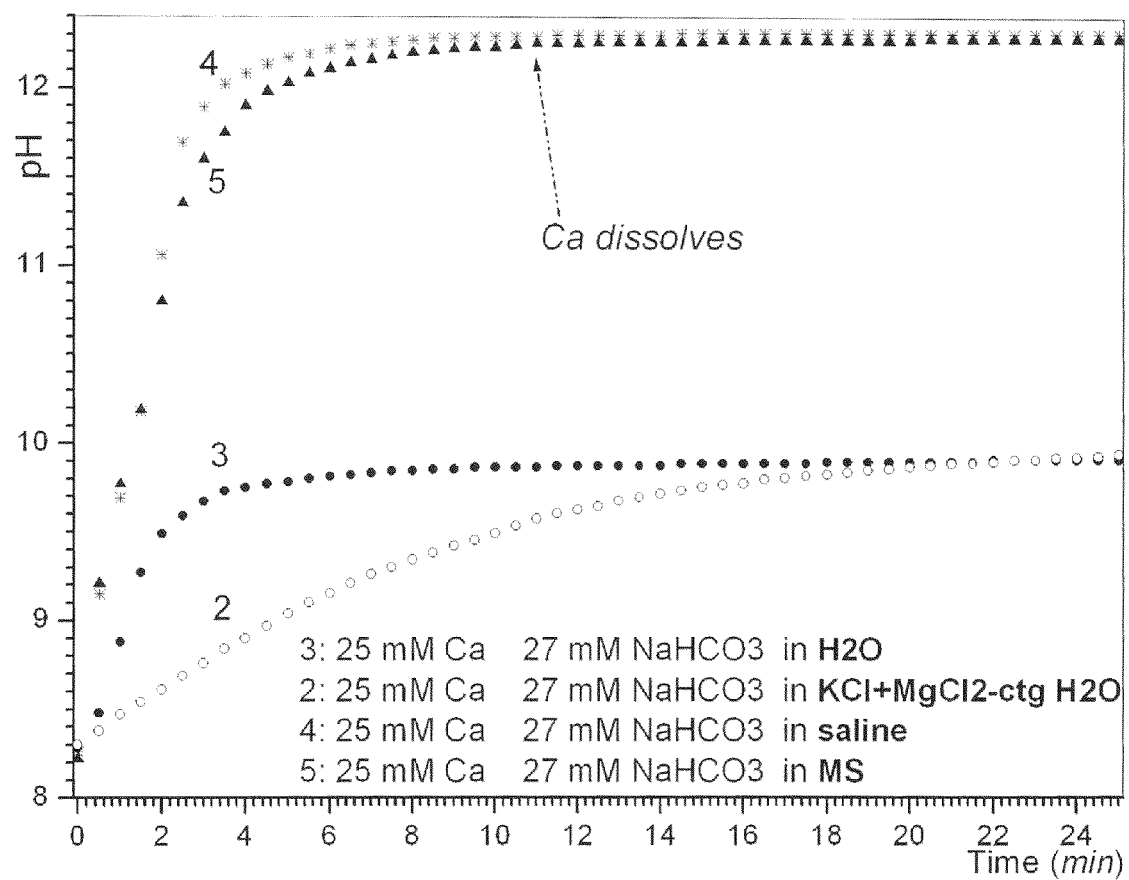

FIG. 2 pH-time curves for experiments 2, 3, 4, and 5 (the moment of dissolution of Ca granules were indicated for experiments 4 and 5)

Figure 3A:
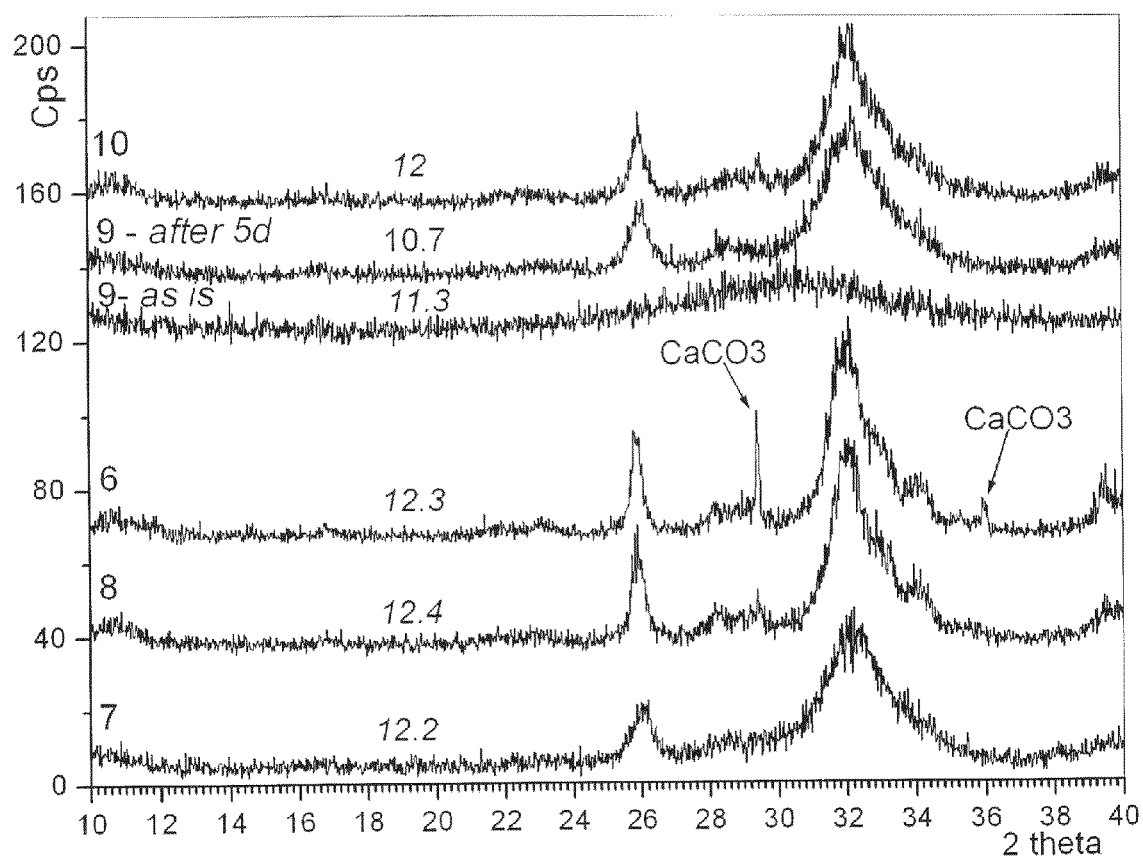

FIG. 3a XRD traces of the samples of experiments 6, 7, 8, 9, and 10 (solution pH values, at the end of 25 min of stirring, were shown on the traces)

Figure 3B:
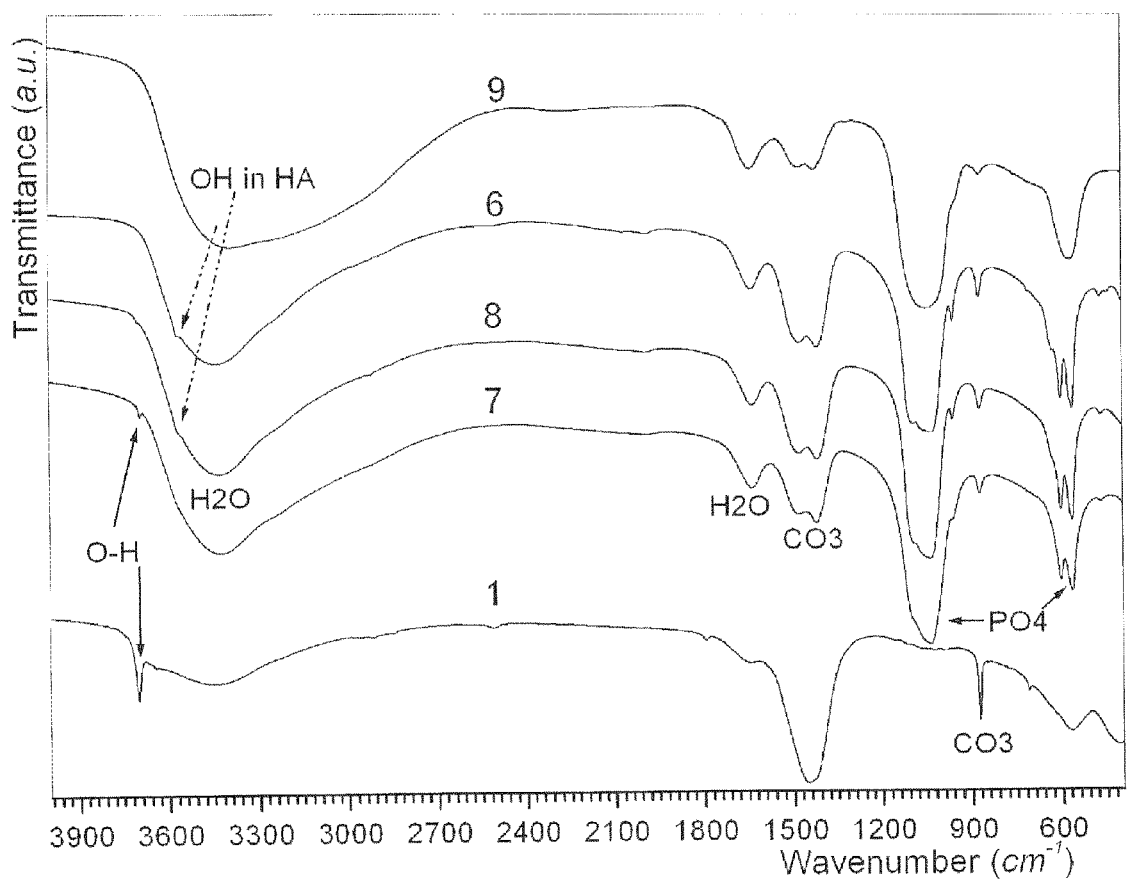

FIG. 3b FTIR traces of the samples of experiments 1, 6, 7, 8, and 9

FIG. 3c pH-time curves for experiments 1, 5, and 8 (the moment of dissolution of Ca granules was indicated by the arrows for experiments 5 and 8)

Figure 4:
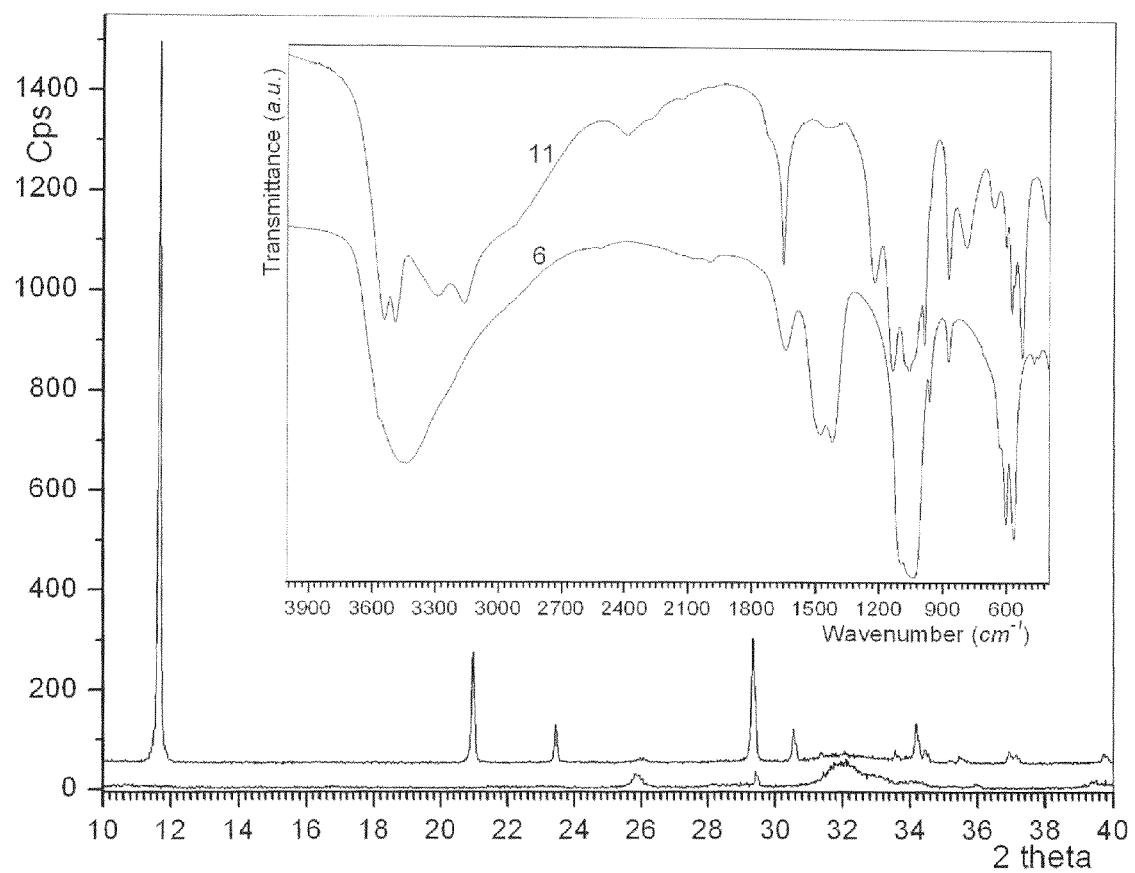

FIG. 4 Combined XRD and FTIR traces for the samples of experiments 6 and 11 (the bottom XRD trace for PCA of experiment 6, the XRD trace for DCPD of experiment 11 shown on top)

Figure 5A:
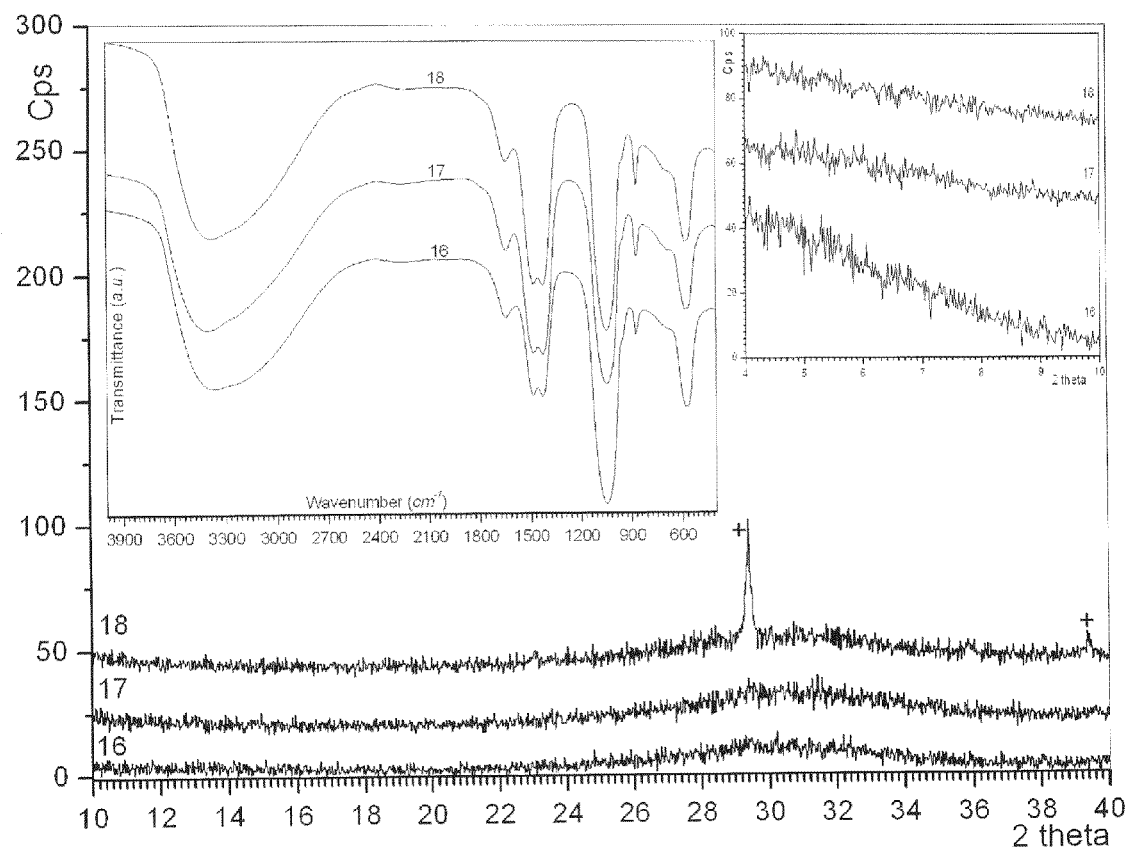

FIG. 5a Combined XRD and FTIR traces for the samples of experiments 16, 17, and 18 ($CaCO_3$ peaks were indicated by + in the XRD trace of experiment 18)

Figure 5B:
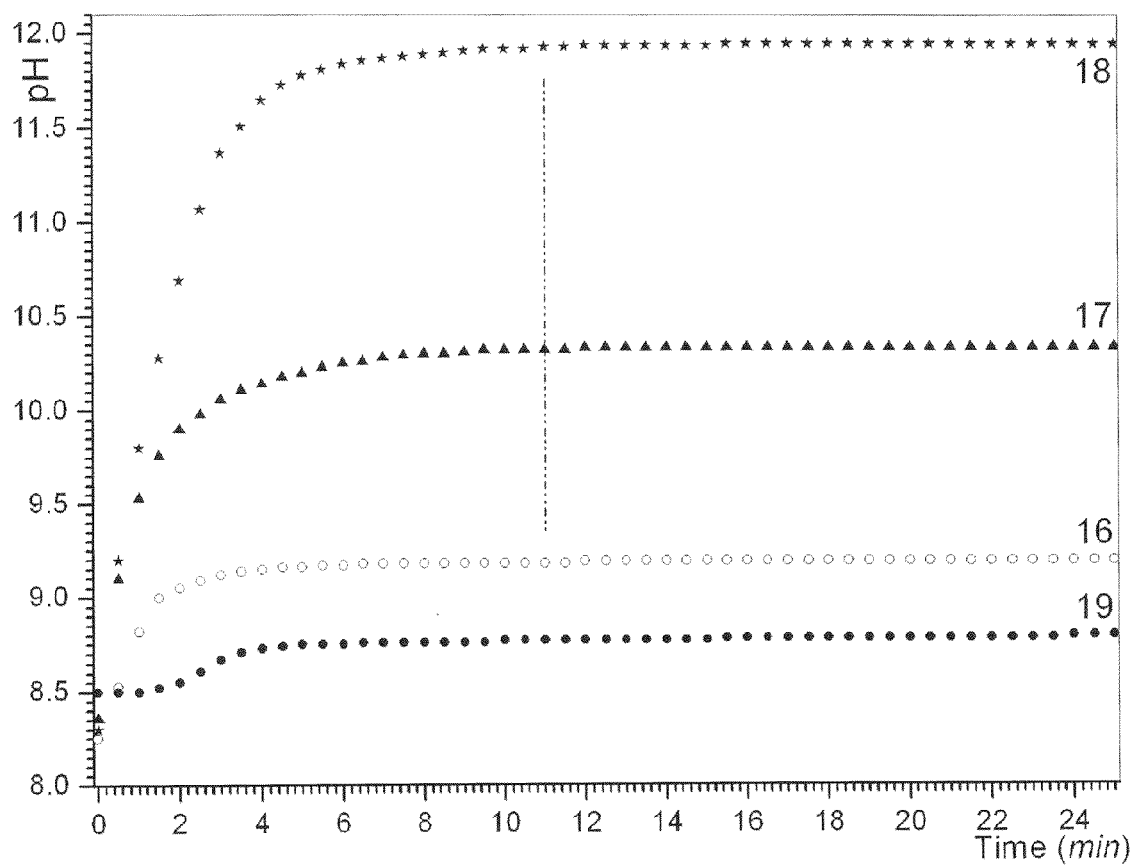

FIG. 5b pH-time curves for experiments 16, 17, 18, and 19 (the dissolution time of Ca granules was indicated by the straight dashed line)

Figure 5C:
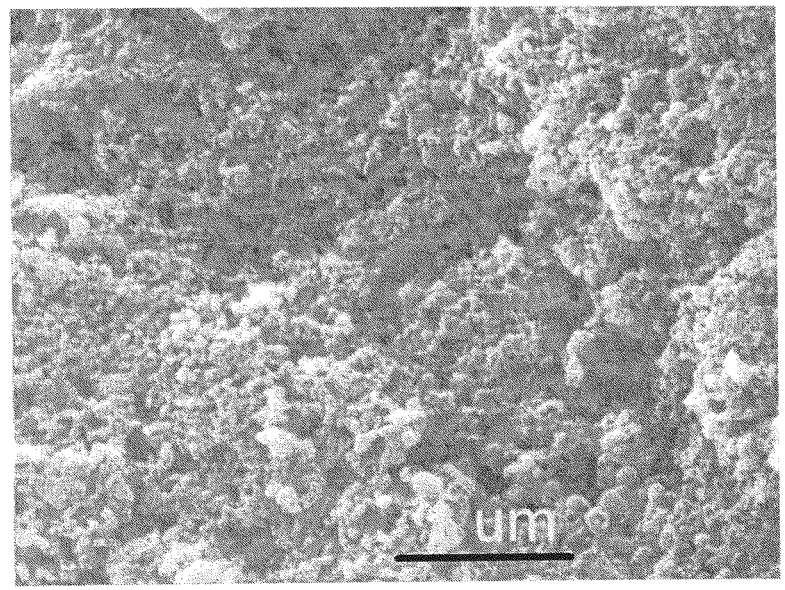

FIG. 5c SEM photomicrograph of the sample of experiment 16

Figure 5D:
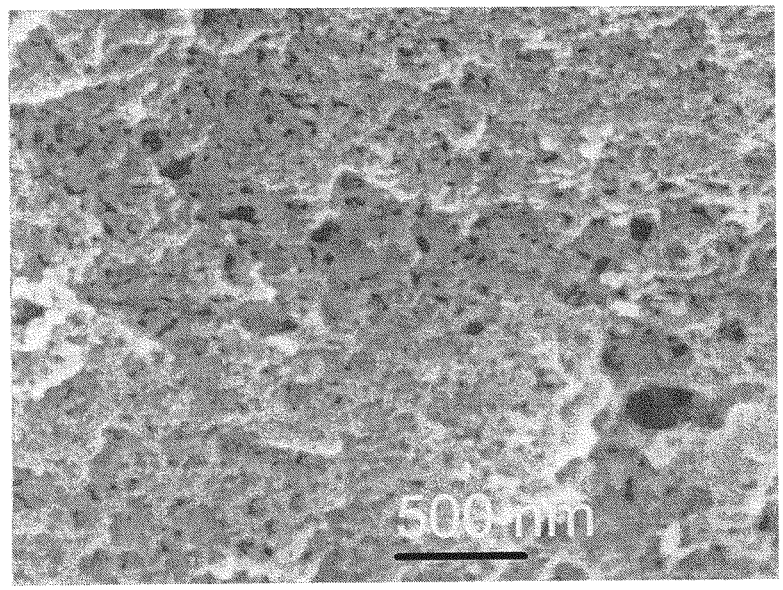

FIG. 5d SEM photomicrograph of the sample of experiment 18

Figure 6:
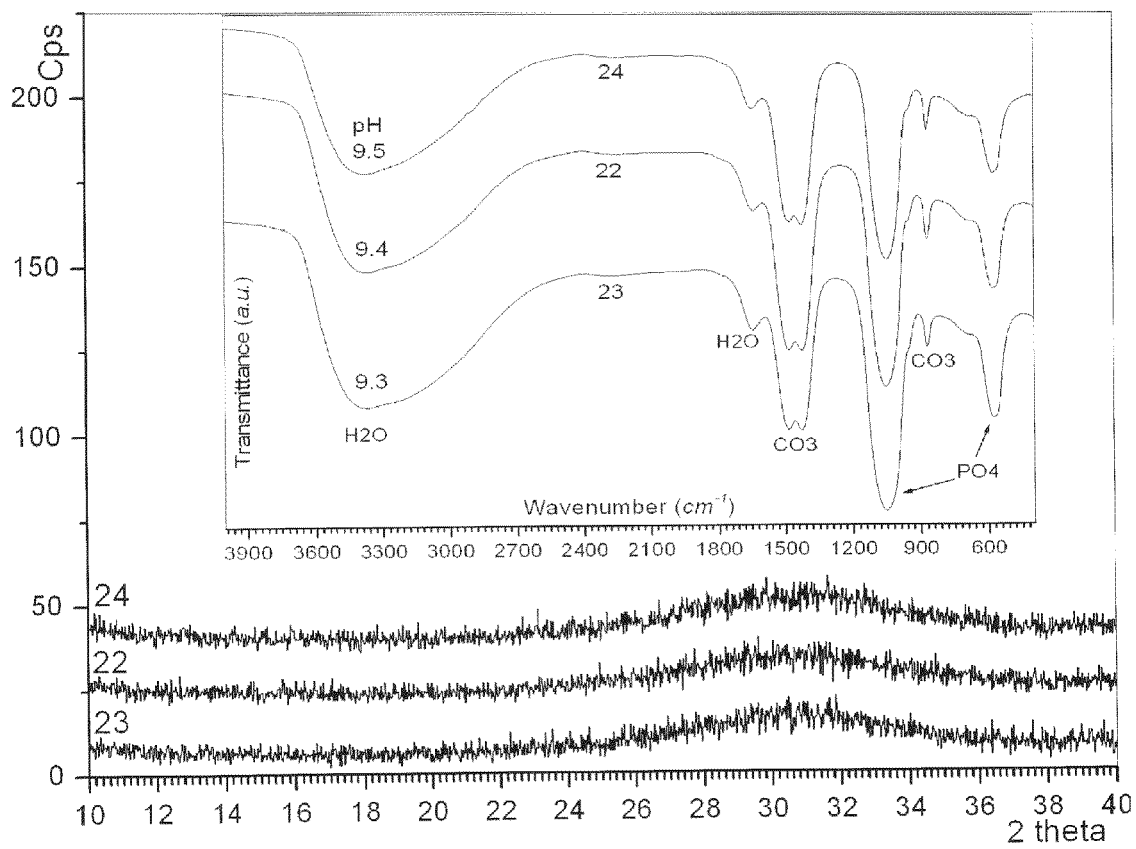

FIG. 6 Combined XRD and FTIR traces for the samples of experiments 22, 23, and 24

Figure 7:
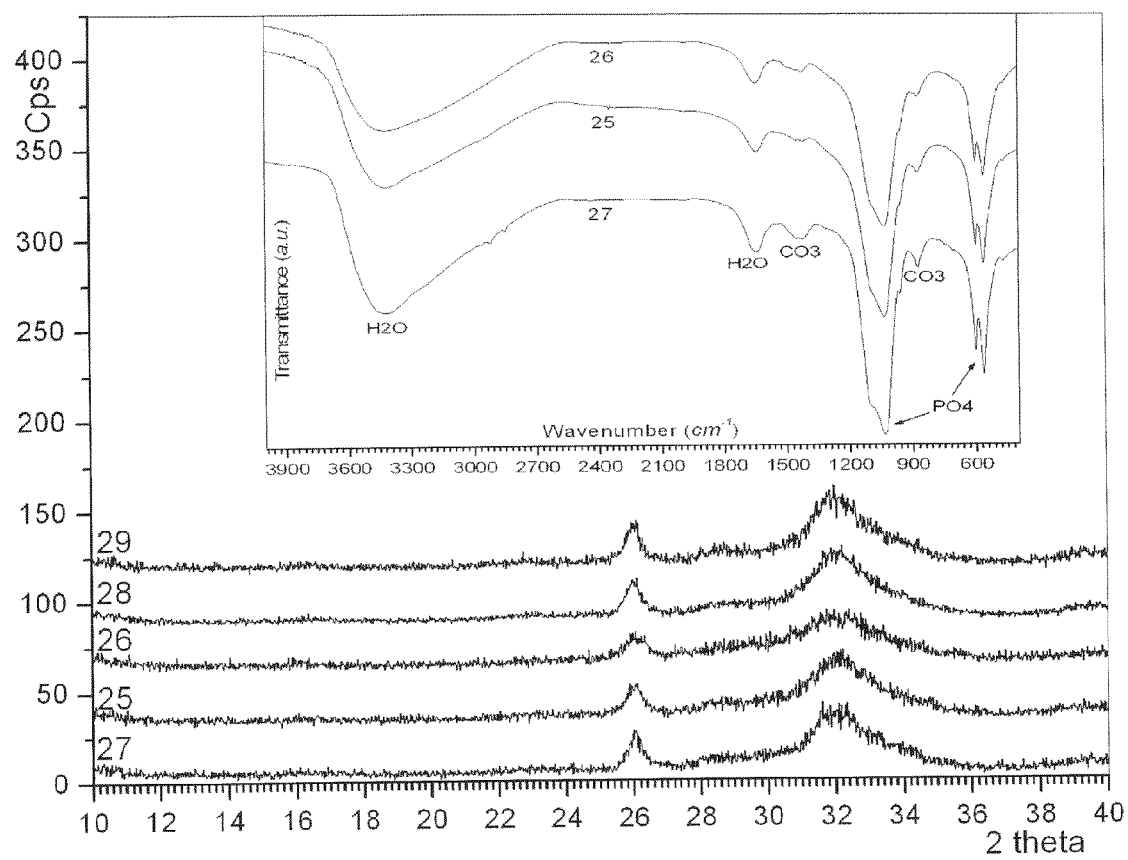

FIG. 7 Combined XRD and FTIR traces for the samples of experiments 25 through 29

Figure 8A:
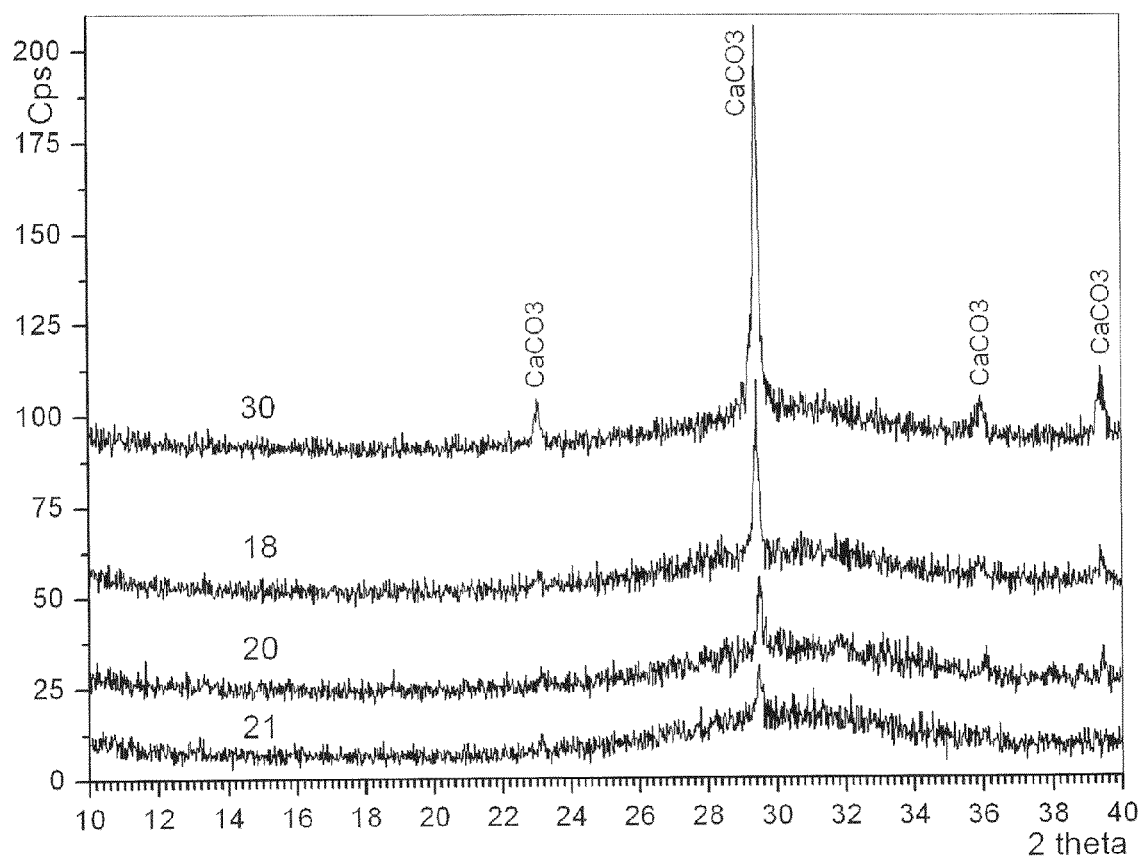

FIG. 8a XRD traces of the samples of experiments 18, 20, 21, and 30

Figure 8B:
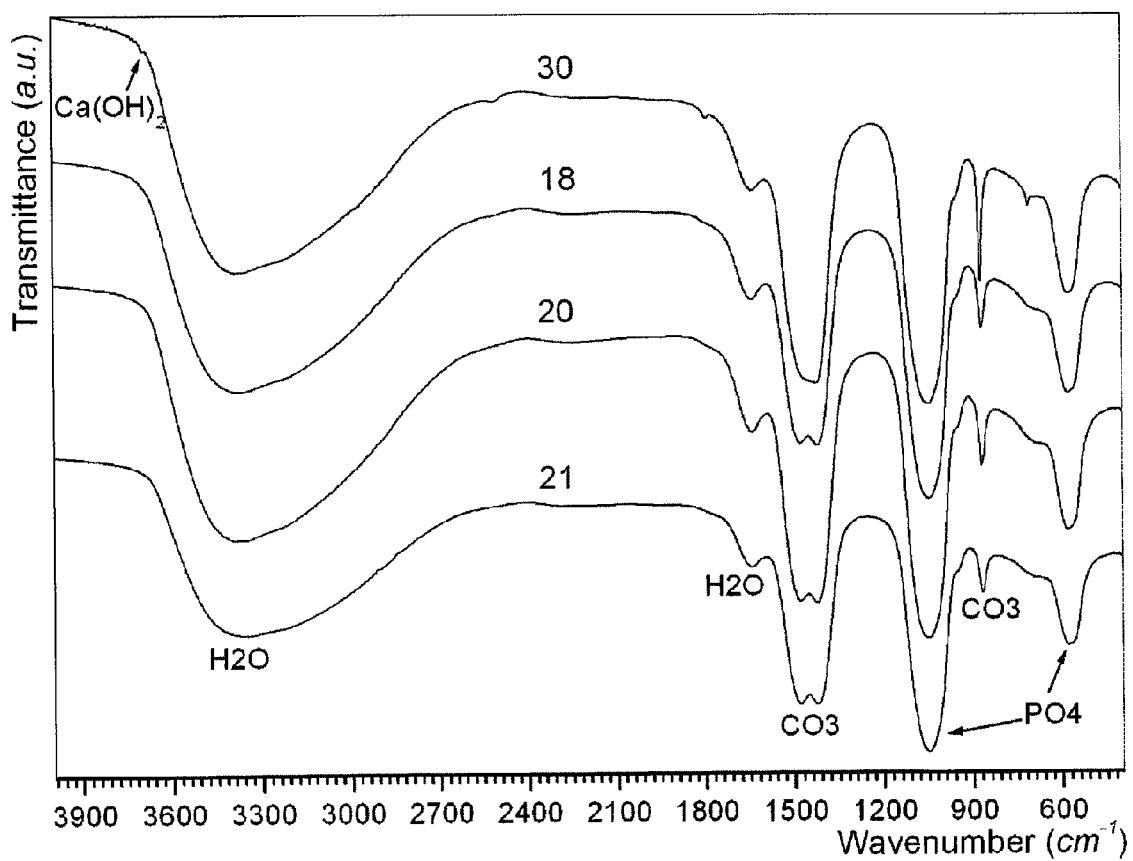

FIG. 8b FTIR traces of the samples of experiments 18, 20, 21, and 30

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLES

Example 1

Solution Preparation and Synthesis

The synthesis solutions were prepared in 500 mL-capacity Pyrex™ glass bottles. Five hundred mL of doubly-distilled water was first placed into the bottles at room temperature (RT, 22±1° C.). The carefully weighed chemicals were added, one by one, to the bottle, under constant stirring of the solution inside. The next chemical was not added prior to the complete dissolution of the previous one. Table 1 shows the procedure of preparing the synthesis/mineralization solutions (MS) in 500 mL distilled water (not boiled prior to use to remove any possible $HCO_3^-$). The chemicals were added in the order given. Table 1 offers three choices of solution preparation; the first one leads to preparing a solution with 10 mM $HPO_4^{2-}$, whereas the third results in a solution with 1 mM $HPO_4^{2-}$. All solutions shown in Table 1 were fully transparent at the time of preparation, and thus they were ready for the addition of the pre-weighed amount of Ca metal (or calcium chloride, calcium acetate monohydrate or calcium nitrate tetrahydrate in a limited number of experiments).

TABLE 1

Preparation of mineralization solutions (MS)

| Chemical | g | mM cation | 500 mL H$_2$O basis mM anion |
|---|---|---|---|
| KCl | 0.1865 | 5 K$^+$ | 5 Cl$^-$ |
| MgCl$_2$·6H$_2$O | 0.1525 | 1.5 Mg$^{2+}$ | 3 Cl$^-$ |
| NaCl | 2.7760 | 95 Na$^+$ | 95 Cl$^-$ |
| NaHCO$_3$ | 1.1341 | 27 Na$^+$ | 27 HCO$_3^-$ |
| Choices: | | | |
| (1) Na$_2$HPO$_4$ | 0.7098 | 20 Na$^+$ | 10 HPO$_4^{2-}$ |
| (2) Na$_2$HPO$_4$ | 0.3549 | 10 Na$^+$ | 5 HPO$_4^{2-}$ |
| (3) Na$_2$HPO$_4$ | 0.0710 | 2 Na$^+$ | 1 HPO$_4^{2-}$ |

To further clarify the solution preparation technique described in Table 1; one first adds KCl to 500 mL of water, dissolves it, then performs the respective additions of MgCl$_2$.6H$_2$O, NaCl and NaHCO$_3$. At that moment, the solutions contain 5 mM K$^+$, 1.5 mM Mg$^{2+}$, 103 mM Cl$^-$, and 27 mM HCO$_3^-$. These on concentrations are identical with those of the blood plasma. If one then adds 0.7098 g of Na$_2$HPO$_4$, the solution has a total Na+ ion concentration equal to 142 mM. This concentration of Na+ is exactly that of the blood plasma. The solution thus obtained according to the choice-1 of Table 1 was able to match the Na$^+$, K$^+$, Mg$^{2+}$, HCO$_3^-$, Cl$_-$ concentrations of the blood plasma, but will possess 10 times the HPO$_4^{2-}$ concentration of plasma. However, the solution of choice-3 (of Table 1) has the identical HPO$_{42-}$ concentration as blood plasma.

If one were using CaCl$_2$.2H$_2$O as the calcium source (instead of Ca metal), it would not be possible to maintain the proper Cl$^-$ ion concentration in the solution, i.e., it would have been in excess of 103 mM. Blood plasma contains exactly 103 mM Cl$^-$. If one were using Ca(NO$_3$)$_2$.4H$_2$O as the calcium source, then the synthesis medium would have contained nitrate ions, which are not present in the blood plasma. The same applies to the use of Ca-acetate as well.

Powder formation began instantly by the addition of prescribed amount of calcium metal granules into the stirred mineralization solutions. Reactions were continued for 25 minutes at RT (22±1° C.). pH values were recorded every 30 seconds, starting from the moment of adding Ca metal into the solutions. At the end of 25 minutes of stirring, the formed solids were immediately and quickly filtered out of their mother liquors by using a Matron No. 2 filter paper via a Buechner funnel apparatus, backed up with a mechanical vacuum pump. The solid residues were washed with 750 mL of distilled water and then dried on watch-glasses at RT for 48 hours in an air-ventilated drying cabin. In the duplicate experiments, samples were synthesized once more as described above, but then left in the solutions overnight (i.e., at least 17 h), in the bottles, at RT. The pH values of the solutions were measured once again after that long period of RT ageing and exactly the same values were found with those measured after only 25 minutes of reaction.

Sample Characterization

Prior to powder X-ray diffraction (XRD) and Fourier-transform infrared spectroscopy (FTIR) analyses, the dried samples were ground, manually, in an agate mortar by using an agate pestle. XRD runs were performed (Advance D8, Bruker, Karlsruhe, Germany) in the step scan mode, with the step size of 0.02° and preset time of 5 seconds. The powder diffractometer was equipped with a Cu tube and operated at 40 kV and 40 mA. XRD samples were prepared by gently packing the powders into the sample holder cavity of around 1 mm-deep. FTIR samples were mixed with Kbr powders at the ratio of 1 mg sample-to-250 mg KBr in an agate mortar. FTIR pellets of 13 mm diameter were pressed at 10 tons. FTIR data were collected (Spectrum One, PerkinElmer, Waltham, Mass.) by using 256 scans. Scanning electron microscopy (Vega-3, Tescan, A. S., Brno, Czech Republic) samples were not ground and the small sample chunks were sputter-coated with a thin gold layer before imaging.

Example 2

Synthesizing $CaCO_3$ by Using Metallic Ca 25 mM (i.e., 10 times the calcium concentration of blood plasma) of Ca metal granules were added:
(i) into water,
(ii) into saline (NaCl—, KCl— and/or $MgCl_2 \cdot 6H_2O$-containing) water, or
(iii) into carbonated ($HCO_3^-$-containing, but no chlorides) water.

Then the granules were stirred at RT in these solutions for 25 minutes. The experiments detailed in Table 2 summarized the design of this study.

Calcium granules stirred in doubly-distilled water for 25 minutes (with a rise in solution pH to around 12) were not dissolved (Experiment-1 of Table 2), they rather seemed to be rapidly covered with a white layer consisting of a biphasic mixture of $Ca(OH)_2$ and $CaCO_3$, as determined by their XRD data given in FIG. 1a. XRD data, only in this case, were collected from the as-recovered granules, without attempting to crush them. One can further speculate here that the incident x-rays would not be able to pass through the hydroxide-carbonate layer formed on the granules to reach their still metallic cores.

25 mM of calcium granules stirred for 25 minutes in an aqueous solution containing only 5 mM $K^+$, 1.5 mM $Mg^{2+}$ and 27 mM $HCO_3^-$ did not totally dissolve. The $Cl^-$ ion concentration of this solution was equal to 8 mM (Experiment-2 of Table 2), but the $K^+$ and $Mg^{2+}$ concentrations were equal to that of blood plasma. Ca granules did not dissolve in distilled water (Exp-1), and they also did not totally dissolve in a solution containing 8 mM $Cl^-$ and 27 mM $HCO_3^-$ (Exp-2). In these two experiments, the rapid formation of a biphasic layer of $Ca(OH)_2$ (major phase) and $CaCO_3$ (minor phase) on the surfaces of the Ca metal granule was observed.

In Exp-3 (Table 2), 25 mM calcium granules were stirred in distilled water containing only 27 mM $Na^+$ and 27 mM $HCO_3^-$ (no $Cl^-$). Granules did not dissolve. Very small amounts of solution precipitates formed in experiments 2 and 3 proved, by XRD and FTIR, to be single-phase $CaCO_3$.

$Cl^-$ concentration was increased to 95 mM in Exp-4. 25 mM of calcium granules stirred in an aqueous solution (Exp-4) containing 122 (=95+27) mM $Na^+$, 95 mM $Cl^-$, and 27 mM $HCO_3^-$ were dissolved completely and produced quite a significant amount of $CaCO_3$ precipitate in the solution in 25 minutes. We have thus experimentally determined that there is a close relationship between the complete dissolution of the

TABLE 2

| Experiment | P source | Ca source | $CO_3$ source | P (mM) | Ca (mM) | $CO_3$ (mM) | Final pH | Phases/XRD | Medium |
|---|---|---|---|---|---|---|---|---|---|
| 1 | — | Ca | — | — | 25 | — | 12.6 | $Ca(OH)_2$ + $CaCO_3$ | $H_2O$ |
| 2 | — | Ca | $NaHCO_3$ | — | 25 | 27 | 9.9 | $CaCO_3$ | 5KCl + 1.5$MgCl_2$ |
| 3 | — | Ca | $NaHCO_3$ | — | 25 | 27 | 9.9 | $CaCO_3$ | $H_2O$ |
| 4 | — | Ca | $NaHCO_3$ | — | 25 | 27 | 12.3 | $CaCO_3$ | 95NaCl |
| 5 | — | Ca | $NaHCO_3$ | — | 25 | 27 | 12.3 | $CaCO_3$ | MS |
| 6 | $Na_2HPO_4$ | Ca | — | 10 | 25 | — | 12.3 | PCA + $CaCO_3$ | $H_2O$ |
| 7 | $Na_2HPO_4$ | Ca | — | 10 | 16.667 | — | 12.2 | PCA | MS w/o $HCO_3$ |
| 8 | $Na_2HPO_4$ | Ca | — | 10 | 25 | — | 12.4 | PCA | MS w/o $HCO_3$ |
| 9 | $(NH_4)_2HPO_4$ | Ca | — | 10 | 16.667 | — | 11.3 | ACP | MS w/o $HCO_3$ |
| 10 | $(NH_4)_2HPO_4$ | Ca | — | 10 | 25 | — | 12.0 | PCA | MS w/o $HCO_3$ |
| 11 | $Na_2HPO_4$ | $CaCl_2 \cdot 2H_2O$ | — | 10 | 25 | — | 5.9 | DCPD + PCA | $H_2O$ |
| 12 | $(NH_4)_2HPO_4$ | $CaCl_2 \cdot 2H_2O$ | — | 10 | 16.667 | — | 6.5 | DCPD | MS w/o $HCO_3$ |
| 13 | $(NH_4)_2HPO_4$ | $CaCl_2 \cdot 2H_2O$ | — | 10 | 25 | — | 6.5 | DCPD + PCA | MS w/o $HCO_3$ |
| 14 | $(NH_4)_2HPO_4$ | $CaCl_2 \cdot 2H_2O$ | — | 10 | 50 | — | 5.7 | DCPD + PCA | MS w/o $HCO_3$ |
| 15 | $(NH_4)_2HPO_4$ | $CaCl_2 \cdot 2H_2O$ | — | 10 | 16.667 | — | 6.1 | DCPD + PCA | $H_2O$ |
| 16 | $Na_2HPO_4$ | Ca | $NaHCO_3$ | 1 | 2.5 | 27 | 9.2 | ACP | MS |
| 17 | $Na_2HPO_4$ | Ca | $NaHCO_3$ | 5 | 12.5 | 27 | 10.3 | ACP | MS |
| 18 | $Na_2HPO_4$ | Ca | $NaHCO_3$ | 10 | 25 | 27 | 12.0 | ACP + $CaCO_3$ | MS |
| 19 | $Na_2HPO_4$ | Ca | $NaHCO_3$ | 10 | 25 | 27 | 9.0 | No ppt[s] | $H_2O$ |
| 20 | $(NH_4)_2HPO_4$ | Ca | $NaHCO_3$ | 10 | 25 | 27 | 10.4 | ACP + $CaCO_3$ | MS |
| 21 | $Na_2HPO_4$ | Ca | $NH_4HCO_3$ | 10 | 25 | 27 | 10.1 | ACP + $CaCO_3$ | MS |
| 22 | $(NH_4)_2HPO_4$ | Ca | $NH_4HCO_3$ | 6.667 | 16.667 | 27 | 9.4 | ACP | MS |
| 23 | $(NH_4)_2HPO_4$ | Ca | $NH_4HCO_3$ | 10 | 16.667 | 27 | 9.3 | ACP | MS |
| 24 | $(NH_4)_2HPO_4$ | Ca | $NH_4HCO_3$ | 10 | 25 | 27 | 9.5 | ACP | MS |
| 25 | $Na_2HPO_4$ | $CaCl_2 \cdot 2H_2O$ | $NaHCO_3$ | 10 | 25 | 27 | 7.0 | PCA | MS |
| 26 | $Na_2HPO_4$ | $CaCl_2 \cdot 2H_2O$ | $NaHCO_3$ | 10 | 25 | 27 | 7.0 | PCA | $H_2O$ |
| 27 | $(NH_4)_2HPO_4$ | $CaCl_2 \cdot 2H_2O$ | $NH_4HCO_3$ | 10 | 25 | 27 | 7.0 | PCA | MS |
| 28 | $Na_2HPO_4$ | Ca-acetate | $NaHCO_3$ | 10 | 25 | 27 | 7.0 | PCA | MS |
| 29 | $Na_2HPO_4$ | Ca-nitrate | $NaHCO_3$ | 10 | 25 | 27 | 7.0 | PCA | MS |
| 30 | $Na_2HPO_4$ | $Ca(OH)_2$ | $NaHCO_3$ | 10 | 25 | 27 | 11.7 | ACP + $CaCO_3$ | MS |

Ca metal granules and Cl⁻ concentration of the solution into which they were placed. Ca metal granules added into aqueous solutions caused the evolution of $H_2$ gas (i.e., in situ deprotonation), but that gas evolution slowed down by the formation of a hydroxide layer on the granule surfaces at low $Cl^-$ concentrations. Moreover, since the granule size used in this study was 2 to 4 mm, that gas evolution was not so fierce.

It is assumed that in solutions containing increased amounts of $Cl^-$, $H_2$ gas evolving at the granule surfaces was creating a microenvironment rich in HCl which could help to prevent the formation of the $Ca(OH)_2$ layer, and with an increase in $Cl^-$ concentration from 0 (Exp-1) to 8 mM (Exp-2), then to 95 mM (Exp-4), the granules were dissolving in increasing amounts.

Experiment-5 was similar to experiment-4 but the MS solution (see Table 1) of Exp-5 also contained $K^+$ (5 mM), $Mg^{2+}$ (1.5 mM), $HCO_3^-$ (27 mM) and $Cl^-$ (103 mM) ions at exactly the human blood plasma levels. Half a gram of starting Ca granules was completely dissolved and produced $CaCO_3$ precipitates (1.228 g) at a high process yield (98.15% of theoretical), The XRD data of the samples of experiments 4 and 5 (not shown) indicated $CaCO_3$ of relatively high crystallinity, individual XRD datum being indistinguishable from one another. However, the FTIR data of $CaCO_3$ produced in MS solution (Exp. 5) was showing the O—H stretching vibration at around 3700 cm⁻¹, as indicated in FIG. 1b. Based on observing the IR band at 1083 cm⁻¹, presence of very small amounts of vaterite may be suspected, although XRD data did not show this phase. The photomicrographs of the starting Ca granules and the calcite precipitated in Exp. 5 were given in FIGS. 1c and 1d, respectively. The calcite crystals formed by adding 25 mM calcium granules into the MS solution (Exp. 5) had a mean particle size of around 5 μm, exhibiting a high degree of agglomeration, displayed nanosize steps and kinks reminding a diffusion-controlled crystal growth kinetics on their surfaces, and by this way, they differed from the clean and smooth-surfaced rhombic morphology of calcite synthesized in distilled water. The first five experiments (of Table-2) also helped to explain why an aqueous solution with a $Cl^-$ concentration close to 100 mM was preferred for use with the Ca metal granules/shots. Human blood plasma contains 103 mM $Cl^{-1}$, therefore, the findings of the first five experiments were also indicating us the way to develop a solution mimicking the ion concentrations of human blood plasma.

FIG. 2 depicted the pH-time curves of the $CaCO_3$ synthesis experiments by using Ca granules. Ca metal granules were completely dissolved in experiments 4 and 5 at exactly the 11$^{th}$ minute. However, this specific time of dissolution would surely depend on the stirring speed (750 rpm) employed, as well as the volume and geometrical shape of glass bottles in which the reactions were performed throughout this study.

All of the above solutions and numbers may seem somewhat complicated at the first sight but they actually point to a very simple fact, which can be explained by the below equations.

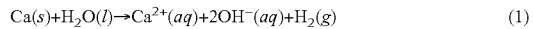

$$Ca(s)+H_2O(l) \rightarrow Ca^{2+}(aq)+2OH^-(aq)+H_2(g) \qquad (1)$$

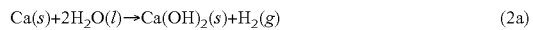

$$Ca(s)+2H_2O(l) \rightarrow Ca(OH)_2(s)+H_2(g) \qquad (2a)$$

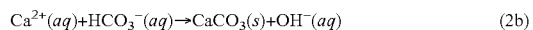

$$Ca^{2+}(aq)+HCO_3^-(aq) \rightarrow CaCO_3(s)+OH^-(aq) \qquad (2b)$$

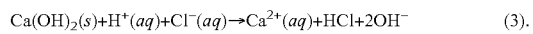

$$Ca(OH)_2(s)+H^+(aq)+Cl^-(aq) \rightarrow Ca^{2+}(aq)+HCl+2OH^- \qquad (3).$$

Equation-1 explains the evolution of H2 gas and the observed rise in pH upon adding the calcium granules into the solutions. Equations (2a) and (2b) explain why the Ca granules did not dissolve in doubly-distilled water, and why the XRD data of FIG. 1 showed $Ca(OH)_2$. Calcium hydroxide, $Ca(OH)_2$, is extremely prone to conversion at its surface to calcite $(CaCO_3)$, and even many "pure," commercial $Ca(OH)_2$ powders have measurable amounts of $CaCO_3$ in them, which can be readily confirmed by a simple FTIR run to be performed on those so-called pure and brand-new $Ca(OH)_2$ samples. Equation 3 explain why the Ca-metal granules readily dissolved in blood plasma-like, mineralization solutions (MS), containing significant amounts (103 mM) of $Cl^-$ ions, in such a short time by causing such a rapid rise in pH.

Example 3

Synthesis of CaP in $HCO_3^-$-Free Solutions by Using Ca Metal

Ca metal shots/granules were not expected to fully react in water only containing $HPO_4^{2-}$ ions. In the absence of $Cl^-$ ions, the granules would be easily covered with Ca-hydroxide and/or Ca-carbonate and would stop reacting. This expectation was tested in experiment 6 (Table 2). 25 mM of calcium granules stirred in water only having 10 mM $Na_2HPO_4$ did not dissolve completely, but the pH of the solution was able to rise above 12 and the small amount of precipitates formed were found, by XRD (FIG. 3a), to be comprised of biphasic mixtures of cryptocrystalline apatitic CaP (PCA) and calcite.

Experiments 7 and 8 were performed to study the effect of Ca/P molar ratio, i.e., 1.667 and 2.50, in reacting Ca granules with the MS solutions free of $HCO_3^-$ ions. Both of these experiments produced cryptocrystalline apatitic calcium phosphate (PCA) samples in solutions with final pH values greater than 12 (FIGS. 3a and 3b), without any calcite. It was important to notice the characteristic stretching vibration of the O—H group at 3571 cm⁻¹ in the IR data (FIG. 3b) of the sample of Exp-8. Carbonates detected in the samples of FIGS. 3a and 3b were due to the small amounts of dissolved $HCO_3^-$ present in the distilled water (not previously boiled) used. Calcium granules reacted completely by the end of the 11$^{th}$ minute as shown in FIG. 3c.

The MS solutions of experiments 7 and 8 had 115 mM $Na^+$, 103 mM $Cl^-$, 5 mM $K^+$, 1.5 mM $Mg^{2+}$ and 10 mM $HPO_4^{2-}$, and in both experiments one is able to freely change the Ca content without disturbing the concentration of any other ion in the solution; i.e., another advantage of using Ca metal in CaP synthesis. This would not be possible if one were using, for instance, $CaCl_2 \cdot 2H_2O$ as the calcium source.

Experiments 7 and 8, therefore, showed a simple way of producing cryptocrystalline (some call it poorly crystalline or poorly crystallized or nanocrystalline) apatitic CaP powders at RT, in a very short 25 minutes, without employing any external pH control technique (such as drop-wise addition of a strong base such as $NH_4OH$, NaOH, KOH, or LiOH) at an in situ solution pH of 12. Exp-8 had the nominal, solution Ca/P molar ratio of 2.5, which was equal to that of blood plasma. Bacteria cannot grow at a solution pH of 12, but they definitely can if the synthesis solutions were at neutral pH (6.8 to 7.6). This is another advantage of using Ca metal in PCA synthesis.

Experiments 9 and 10 (Table 2) were replacing the $Na_2HPO_4$ used in experiments 7 and 8 with $(NH_4)_2HPO_4$, while keeping all the other synthesis parameters unchanged. Although the presence of $NH_4$ ions in a synthesis system claiming to mimic the ions and on concentrations in blood plasma would not be acceptable, experiment 9 produced amorphous calcium phosphate (ACP) at the Ca/P molar ratio of 1.667 and the final pH value of 11.3.

It was quite easy to distinguish between the ACP and PCA phases by using their FTIR data, as exemplified by the IR traces of experiments 9 and 7 in FIG. 3b, respectively. In the IR data of ACP samples the phosphate bands over the range of 660 to 490 cm$^{-1}$ do not show that splitting, which was otherwise observed in PCA samples. When the Ca/P molar ratio was increased to 2.5 in experiment 10, the produced powders were not ACP but PCA. The solution pH in this experiment was 12. Upon repeating the experiment 9, but ageing the formed precipitates in the mother solution for 5 days at RT (solution pH dropping to 10.7 from 11.3, in 5 days), followed by filtering and drying, the obtained powders were consisted of PCA, not ACP, as shown in FIG. 3a. This was quite an expected result since ACP was not a stable phase (even in its mother liquor over a period of 5 days) and it acted as a precursor to PCA.

Comparative Example 4

Synthesis of CaP in $HCO_3^-$-Free Solutions by Using $CaCl_2.2H_2O$ Instead of Ca Metal Upon replacing the Ca metal with $CaCl_2.2H_2O$, the pH values of synthesis solutions drastically suffered from this change. Experiment 11 in comparison to experiment 6 showed that drastic drop in solution pH from 12.3 to 5.9. At such a low pH (5.9), it was inevitable to form DCPD (dicalcium phosphate dihydrate; brushite; $CaHPO_4.2H_2O$). The comparison of the XRD and FTIR data of experiments 6 (with Ca metal in water) and 11 (with Ca-chloride in water) is given in FIG. 4.

Experiments 12 through 15 tested the formation of calcium phosphates in water and $HCO_3^-$-free MS solutions by using Ca-chloride and diammonium hydrogen phosphate as the starting chemicals. In these experiments solution pH values remained between 5.7 and 6.5, and the obtained precipitates contained DCPD as the major phase.

If one used Ca-chloride dihydrate instead of Ca metal, as the calcium source, to synthesize CaP in $HCO_3^-$-free plasma-like solutions, mildly acidic DCPD would be the major phase obtained.

Example 5

Synthesis of ACP in MS Solutions by Using Ca Metal

Experiments 16 through 18 tested the synthesis conditions closest to the ionic concentrations of the human blood plasma, by using metallic Ca granules. In experiment 16; calcium, phosphate ($HPO_4^{2-}$), bicarbonate ($HCO_3^-$), potassium, chloride, and magnesium on concentrations were made identical with that of blood plasma, but in that experiment the sodium concentration was equal to 124 mM. In experiment 18, on the other hand; bicarbonate (27 mM), sodium (142 mM), magnesium (1.5 mM), potassium (5 mM) and chloride (103 mM) ion concentrations were identical with that of blood plasma. In other words, experiments 16 through 18 tested the MS solutions given in Table 1 under three different choices. The combined XRD and FTIR data of the resultant ACP samples were given in FIG. 5a. The second inset of FIG. 5a confirmed the absence of the octacalcium phosphate (OCP, $Ca_8(HPO_4)_2(PO_4)_4.5H_2O$) phase in the samples of experiments 16 to 18. At such high solution pH values it would be very difficult, if not impossible at all, to observe acidic OCR The sample of experiment 18 showed the presence of a small amount of calcite ($CaCO_3$) phase in its XRD data. However, when we duplicated experiments 16 through 18, and left the precipitate containing solutions overnight without stirring, followed by filtering and drying, the resultant XRD data of especially experiment 18 did not show that second phase of calcite. All three samples (16 through 18) depicted the characteristic XRD pattern of ACP. The Ca metal granules in experiments 16 through 18 all dissolved/disappeared at around the 11$^{th}$ minute. When experiment 18 is performed (i.e., experiment 19) in doubly-distilled water (containing 10 mM $HPO_4^{2-}$, 27 mM $HCO_3^-$, and 47 mM $Na^+$), instead of the MS solution, Ca metal granules did not dissolve and no precipitates were obtained. This again proved the role of Cl$^-$ ions, as explained by equations (1) through (3) above.

FIG. 5b showed the pH-time curves for experiments 16 through 19. The curves for experiments 16 through 18 in this figure, as well as the previous pH-time curves (FIG. 3c), exhibited a nonlinear increase of pH in a time dependent manner and they were approximated (TableCurve, v1.10, Jandel Scientific. 1993) by the logistic dose response function $(y=a+[b/(1+(x/c)_d)])$, for which the experimental parameters were given below in Table 3.

The SEM photomicrographs of samples obtained from experiments 16 and 18, were given in FIGS. 5c and 5d, respectively. It should be noted that these are filtered and dried samples, they were not even lyophilized upon separation from their mother liquors. Regular drying causes agglomeration of individual particles or moieties.

TABLE 3

Results of logistic dose-response curve fitting on the pH-time curves

| Parameters | Exp 16 | Exp 17 | Exp 18 | Exp 8 | Exp 5 |
| --- | --- | --- | --- | --- | --- |
| a | 8.2495 | 8.3653 | 8.4338 | 12.6960 | 8.4163 |
| b | 0.9421 | 2.0039 | 3.5657 | −3.7066 | 3.9064 |
| c | 0.7841 | 0.7827 | 1.3204 | 0.0222 | 1.4376 |
| d | −1.9020 | −1.3032 | −1.7912 | 0.4083 | −1.8735 |
| r$^2$ | 0.9994 | 0.9985 | 0.9936 | 0.9794 | 0.9922 |
| Fit Std. Error | 0.0043 | 0.0139 | 0.0608 | 0.0739 | 0.0760 |

Nevertheless, it was apparent from FIGS. 5c and 5d that the average particle diameter in these x-ray amorphous, carbonated and mesoporous CaP powders was pretty much less than 70 nm. This is the particle size directly observed by the SEM, not the crystallite size. Crystallite sizes cannot be determined by using the Scherrer equation while using the XRD data of x-ray amorphous samples (FIG. 5a).

The concentration of Ca metal added into the MS solutions (starting from 2.5 mM in experiment 16 and going up to 25 mM in experiment 18) was found to be quite influential on the final pH values attained in syntheses. When the Ca concentration was kept equal to that of the blood plasma (i.e., 2.5 mM in exp. 16), the pH of the solution has risen only to 9.2 and stabilized at that value. By increasing it to 12.5 mM (i.e., 5 times that of plasma in exp. 17), the pH rose to 10.3, and the pH increased to 12 when the Ca concentration in the MS solution was increased to ten times that of the blood plasma (exp. 18).

The conditions of Exp-16 was of pivotal significance for this study, since the $Ca^{2+}$, $HPO_4^{2-}$, $HCO_3^-$, $Mg^{2+}$, $K^+$, $Cl^-$ concentrations of this experiment were identical with those of human blood, and moreover, no foreign ions such as nitrate, ammonium and acetate were introduced to the synthesis process. As shown by the data of FIG. 5b, maintaining a literally constant pH in CaP synthesis, without employing any pH control (such as adding bases or acids to keep the pH constant), was never shown before to be possible. These define the novelty and practicality of the approach of using Ca metal as the sole calcium source in CaP synthesis.

Example 6

Synthesis of ACP in MS Solutions by Using Ca Metal, Ammonium Phosphates and Ammonium Carbonate The influence of the use of $(NH_4)_2HPO_4$ and $NH_4HCO_3$ salts, instead of $Na_2HPO_1$ and $NaHCO_3$ were also tested in synthesizing CaP powders by using Ca metal granules. Experiments 20 through 24 (of Table 2) all produced ACP powders in MS solutions. The use of Na-phosphate or Na-bicarbonate (as shown in experiments 20 and 21) kept the solution pH at above 10, but when both of $Na_2HPO_4$ and $NaHCO_3$ were replaced by $(NH_4)_2HPO_4$ and $NH_4HCO_3$ the solution pH values dropped to about 9.3 to 9.5 (experiments 22 through 24). Of course, the solutions used in these experiments could not mimic the physiological solutions, since they contained significant amounts of ammonium ions which are not found in blood plasma. The XRD and FTIR data of experiments 22 through 24 were shown in FIG. 6. However, the direct comparison of Exp-18 and Exp-24 would yield that it would be possible to produce carbonated ACP powders, by using Ca metal, at pH values of 12 and 9.5, respectively, without using any external pH adjustment controls.

Comparative Example 7

Synthesis of PCA in MS Solutions at pH 7 without Using Ca Metal

Experiments 25 through 30 of Table 2 studied the synthesis of CaP in MS solutions, without using Ca metal. These experiments were planned to show what difference the use of Ca metal would really cause in comparison to the more commonly used calcium on sources, such as $CaCl_2.2H_2O$, calcium acetate monohydrate $(Ca(CH_3CO_2)_2.H_2O)$, $Ca(NO_3)_2.4H_2O$, and $Ca(OH)_2$. FIG. 7 showed the XRD traces of samples obtained in experiments 25 through 29, all indicating PCA. The inset in FIG. 7, on the other hand, exhibited the IR traces of the samples of experiments 25 through 27. The IR traces of experiments 26, 28 and 29 were very similar to one another, and they all exhibited much less carbonate on presence (according to the qualitative IR data) in comparison to, for instance, the sample of experiment 27.

MS solutions were working perfectly well, at the stated on concentrations, in providing a reaction pH of exactly 7.0 for Ca-chloride, Ca-acetate, or Ca-nitrate; without a need for any external pH adjustments by acids or bases of any kind. Ca metal granules made it possible to synthesize ACP or PCA powders at pH values higher than 7.0, without needing any base additions for pH control, in MS solutions.

To synthesize PCA by using Ca metal granules, we found that one needed to eliminate $HCO_{3-}$ from the MS solutions. Using $CaCl_2.2H_2O$ in doubly-distilled water or $HCO_3^-$-free MS solutions containing phosphate ions, without any pH adjustments, would never allow the synthesis of PCA, since the pH of the solutions were lower than neutral (i.e., 7) and would thus only be suitable for the crystallization of brushite $(CaHPO_4.2H_2O)$ phase, as also shown in this study.

Example 8

Ca Metal Granules or $Ca(OH)_2$ in MS Solutions?

XRD and FTIR analysis of the sample obtained in experiment 30 (Table 2), which opted for 25 mM $Ca(OH)_2$ to be added into the typical MS solution of this study, tried to provide an answer to the question of this Example. FIG. 8a compared the XRD traces of all the samples of this study which comprised of a biphasic mixture of ACP and $CaCO_3$ after 25 minutes of stirring at RT in the MS solutions. The main comparison should actually be made between the sample 18 (25 mM Ca) and sample 30 (25 mM $Ca(OH)_2$) in the chart of FIG. 8a, since ammonium ions were present in the solutions of sample 20 and 21. Solution-wise, samples 20 and 21 do not compare well with those of samples 18 and 30. When Ca metal in experiment 18 was replaced by $Ca(OH)_2$ in experiment 30, while keeping all the other synthesis parameters constant, the amount of the secondary phase of $CaCO_3$ significantly increased (FIG. 8a). The FTIR data of the same experiments were given in FIG. 8b. FIG. 8b provided the evidence that the sample of experiment 30 was also poisoned with unreacted $Ca(OH)_2$, i.e., presence of the $Ca(OH)_2$-specific IR band recorded at around 3650 $cm^{-1}$. Moreover, the sample of experiment 30 showed the characteristic IR bands of the calcite phase at 2513, 1798, 875 and 712 $cm^{-1}$. In the duplicate experiments same results were obtained meaning that Ca-hydroxide was not able to completely react to form ACP in the MS solutions by fully consuming itself.

Example 9

Significance of Synthesizing CaP in Mineralization Solutions Free of Tris or Hepes Human blood, which provides the necessary nutrients to the trabecular/cancellous bones and the dentine of teeth, does not contain Tris (or Hepes), nitrate, acetate and/or ammonium ions. Therefore, it would be difficult to classify the synthesis (or coating) processes using Tris-HCl (or Hepes-NaOH) buffered solutions and especially the synthesis methods using one or more of the starting chemicals of Ca-nitrate tetrahydrate, Ca-acetate monohydrate, ammonium hydroxide, diammonium hydrogen phosphate or ammonium dihydrogen phosphate as properly mimicking the physiological processes.

Ammonium-, nitrate- and acetate-free synthesis recipes (especially those of experiments 7, 8, 16, 17 and 18) given in Table 2 of this study provided easy-to-reproduce and quite simple procedures to synthesize PCA (cryptocrystalline apatitic CaP) and ACP (x-ray amorphous CaP) powders at RT in glass media bottles, without requiring special reactor designs and pH adjustment/control measures. The PCA or ACP synthesized in such blood plasma-like solutions contain ionic substitutions of $Na^+$, $K^+$, $Mg^{2+}$, $CO_3^{2-}$ and $Cl^-$ ions at the crystallographic Ca, $PO_4$ and OH sites of hydroxyapatite structure. Such ions can be identified by ICP-AES (inductively-coupled plasma atomic emission spectroscopy) analyses.

The ionic strength of the synthesis solutions (after the addition of Ca metal granules) of experiments 7, 8, 16, 17 and 18 of this study was adjusted to be 167.83, 184.5, 139.5, 171.5 and 211.5 mM, respectively. If one were to prepare an aqueous solution comprising 2.5 mM $Ca_{2+}$, 1 mM $HPO_4^{2-}$, 142 mM $Na^+$, 5 mM $K^+$, 1.5 mM $Mg^{2+}$, 27 mM $HCO_3^-$ and 103 mM $Cl^-$ (i.e., the exact on concentrations of human blood plasma) then the ionic strength of that solution would have been 148.5 mM. The ionic strengths higher than 148.5 mM were intentionally chosen in this study to facilitate the synthesis of larger amounts of PCA or ACP powders.

Example 10

ACP Synthesis by Using High Purity Ca Metal Wire

An unused, sterile plastic Eppendorf vial, with a cap, of 5 mL capacity was used to contain 5 mL of MS solution. The MS solution conformed to choice 1 indicated in Table 1 by containing 10 mM $HPO_4^{2-}$ anions previously dissolved in that solution. A piece of calcium wire (99.99% pure, 1 mm in diameter) cut to the proper size that it shall correspond to 25 mM Ca upon total reaction with that 5 mL aliquot of MS solution contained in that Eppendorf vial. Drop-by-drop slow pouring of that solution onto the Ca wire contained in a sterile plastic boat either made it transform into ACP within 3 to 5 minutes, or alternatively, the dropping of that Ca metal wire piece into the Eppendorf vial, tightly closing its cap and ultrasonicating the sealed Eppendorf vial in an ultrasonic bath (upon placing the plastic Eppendorf vial into a small glass beaker filled with deionized water before insertion into the ultrasonic bath) for 3 to 5 minutes caused the in situ formation of a suspension of ACP nanoparticles in the MS solution. Calcium wires can be given numerous shapes other than conventional longitudinal wire geometry before reacting and transforming those into ACP via ultrasonication in such Eppendorf vials.

All patents, publications and abstracts cited above are incorporated herein by reference in theft entirety. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the present invention as defined in the following claims.

The invention claimed is:

1. A method of preparing either calcium phosphates, calcium carbonates, or mixtures thereof, comprising:
   preparing a starting aqueous solution comprising all of 80-150 mM $Na^+$, 0.5-5 mM $K^+$, 1-5 mM $Mg^{2+}$ and 90-125 mM $Cl^-$ ions, and one or more of 4-30 mM carbonate and 0.1-20 mM phosphate; and,
   adding calcium metal into the aqueous solution in an amount of 0.25-50 millimoles of calcium metal per liter of starting aqueous solution to autogeneously precipitate calcium phosphates, calcium carbonates or mixtures thereof,
   wherein the pH of the solution after the reaction is from pH 8 to pH 13,
   wherein the carbonate added to the starting aqueous solution is selected from the group consisting of $CO_3^{2-}$, $HCO_3^-$, $H_2CO_3$, and combinations thereof; and
   wherein the phosphate added to the starting aqueous solution is selected from the group consisting of $PO_4^{3-}$, $HPO_4^{2-}$, $H_2PO_4^-$, $H_3PO_4$ and combinations thereof.

2. The method of claim 1, wherein the calcium phosphates are either amorphous calcium phosphate (ACP) powders or poorly crystallized cryptocrystalline apatite (PCA) powders, and the calcium carbonates are $CaCO_3$ powders.

3. The method of claim 1, wherein the starting aqueous solution further comprises at least one of zinc ions and fluoride ions.

4. The method of claim 1, wherein no hydroxide base is added to the starting aqueous solution.

5. The method of claim 1, wherein none of the hydroxide bases of $NH_4OH$, LiOH, NaOH, KOH, $Mg(OH)_2$ and $Ca(OH)_2$ are added to the starting aqueous solution.

6. The method of claim 1, wherein the pH of the solution after the reaction is from pH 9 to pH 12.

* * * * *